(12) United States Patent
Crane, III et al.

(10) Patent No.: US 6,713,665 B2
(45) Date of Patent: Mar. 30, 2004

(54) MAIZE NPR1 PROMOTER AND METHODS OF USE IN PLANT GENE EXPRESSION

(75) Inventors: Edmund H. Crane, III, Des Moines, IA (US); Douglas A. Rice, Des Moines, IA (US)

(73) Assignee: Pioneer Hi-Bred International, Inc., Des Moines, IA (US)

(*) Notice: Subject to any disclaimer, the term of this patent is extended or adjusted under 35 U.S.C. 154(b) by 40 days.

(21) Appl. No.: 10/047,593

(22) Filed: Jan. 15, 2002

(65) Prior Publication Data

US 2002/0170094 A1 Nov. 14, 2002

Related U.S. Application Data

(62) Division of application No. 09/551,778, filed on Apr. 18, 2000, now Pat. No. 6,504,084.
(60) Provisional application No. 60/130,692, filed on Apr. 23, 1999.

(51) Int. Cl.$^7$ .............................. A01H 5/00; A01H 5/10; C12N 15/04; C12N 15/82; C12N 15/11

(52) U.S. Cl. ..................... 800/298; 800/279; 800/278; 435/320.1; 435/419; 536/24.1

(58) Field of Search ............................... 800/298, 278, 800/279, 302, 301, 300; 435/320.1, 419, 418, 430; 536/24.1

(56) References Cited

U.S. PATENT DOCUMENTS

| | | | |
|---|---|---|---|
| 5,792,904 A | | 8/1998 | Ryals et al. |
| 5,986,082 A | * | 11/1999 | Uknes et al. .............. 800/279 |

FOREIGN PATENT DOCUMENTS

| | | |
|---|---|---|
| WO | WO 97/49822 A1 | 12/1997 |
| WO | WO 98/06748 A1 | 2/1998 |
| WO | WO 98/26082 A1 | 6/1998 |
| WO | WO 99/14350 A1 | 3/1999 |
| WO | WO 00/28036 A2 | 5/2000 |

OTHER PUBLICATIONS

Maiti et al, 1997, Transgen. Res., 6:143–156.*
Donald et al, 1990, EMBO J. 9:1717–1726.*
Chen et al, 2000, Sex. Plant Reprod. 13:85–94.*
Benfrey et al, 1990, Science 250:959–966.*
Kim et al,1994, Plant Mol. Biol. 24:105–117.*
SanMiguel et al, 1998, GenBank Accession No. AF050451.*
Quayle et al, 1992, GenBank Accession No. X58700.*
Cao, et al., 1997, *Cell*, 88: 57–63, "The Arabidopsis NPR1 Gene that Controls Systemic Acquired Resistance Encodes a Novel Protein Containing Ankyrin Repeats".
Cao, et al., 1994, *The Plant Cell*, 6: 1583–1592, "Characterization of an Arabidopsis Mutant That Is Nonresponsive to Inducers of Systemic Acquired Resistance".

Volko, et al., 1998, *Genetics*, 149: 537–548, "Isolation of New Arabidopsis Mutants With Enhanced Disease Susceptibility to *Pseudomonas syringae* by Direct Screening".
Shah, et al., 1997, *MPMI*, 10(1):69–78, "Characterization of a Salicylic Acid–Insensitive Mutant (sail) of *Arabidopsis thaliana*, Identified in a Selective Screen Utilizing the SA–Inducible Expression of the tms2 Gene".
Delaney, et al., 1995, *Proc. Natl. Acad. Sci. USA*, 92: 6602–6606, "Arabidopsis signal transduction mutant defective in chemically and biologically induced disease resistance".
Cao, et al., 1998, *Proc. Natl. Acad. Sci. USA*, 95:6531–6536, "Generation of broad–spectrum disease resistance by overexpression of an essential regulatory gene in systemic acquired resistance".
Ryals, et al., 1997, *The Plant Cell*, 9: 425–439, "The Arabidoipsis NIMI Protein Shows Homology to the Mammalian Transcription Factor Inhibitor IKB".
Glazebrook, et al., 1996, *Genetics*, 143: 973–982, "Isolation of Arabidopsis Mutants With Enhanced Disease Susceptibility by Direct Screening".
Bowling, et al., 1997, *Plant Cell*, 9: 1573–1584, "The cpr5 Mutant of Arabidopsis Expresses Both NPR–1 Dependent and NPR1–Independent Resistance".
Buell, C. Robin, 1998, *Plant Physiol. Biochem*, 36(1–2): 177–186, "Arabidopsis: A weed leading the field of plant–pathogen interactions".
Clarke, et al., 1998, *Plant Cell*, 10: 557–569, "Uncoupling PR Gene Expression from NPR1 and Bacterial Resistance: Characterization of the Dominant Arabidopsis cpr6–1 Mutant".
He, et al., 1998, *Plant J.*, 14(1): 55–63, "Requirement for the induced expression of a cell wall associated receptor kinase for survival during the pathogen response".
Pieterse, et al., 1998, *Plant Cell*, 10: 1571–1580, "A Novel Signaling Pathway Controlling Induced Systemic Resistance in Arabidopsis".

(List continued on next page.)

*Primary Examiner*—Amy J. Nelson
*Assistant Examiner*—Anne Kubelik
(74) *Attorney, Agent, or Firm*—Pioneer Hi-Bred International, Inc.

(57) ABSTRACT

The invention provides isolated NPR1 nucleic acids and their encoded proteins. The present invention provides methods and compositions relating to altering NPR1 concentration and/or composition of plants. The invention further provides recombinant expression cassettes, host cells, and transgenic plants. Additionally, the present invention provides NPR1 promoter elements capable of initiating constitutive expression in a plant expression constructs comprising them, cells, plants and seeds comprising the constructs, and methods of using them to express heterologous nucleic acids in a plant. Further, the present invention provides for methods for screening putative activators of a plant resistance pathway.

10 Claims, 2 Drawing Sheets

OTHER PUBLICATIONS

Reuber, et al., 1998, *Plant J.*, 16(4): 473–485, "Correlation of defense gene induction defects with powdery mildrew susceptibility in Arabidopsis enhanced disease susceptibility mutants".

Simons, et al., 1999, *Plant Phys.*, 120: 529–538, "Enhanced Expression and Activation of the Alternative Oxidase during Infection of Arabidopsis with *Pseudomonas syringae* pv tomato‖".

Shah, et al., 1999, *Plant Cell*, 11: 191–206, "The Arabidopsis ssi1 Mutation Restores Pathogenesis–Related Gene Expression in npr1 Plants and Renders Defensin Gene Expression Salicylic Acid Dependent".

Zhang, et al., 1999, *Proc. Natl. Acad. Sci. USA*, 96: 6523–6528, "Interaction of NPR1 with basic leucine zipper protein transcription factors that bind sequences required for salicylic acid induction of the PR–1 gene".

Molina, et al., 1999, *Plant J.*, 17(6): 667–678, "Inhibition of protoporphyrinogen oxidase expression in Arabidopsis causes a lesion–mimic phenotype that induces systemic acquired resistance".

Dong, et al., 1999, *Plant J.*, 20(2): 207–215, "Harpin induces disease resistance in Arabidopsis through the systemic acquired resistance pathway mediated by salicylic acid and the NIMI gene".

Kachroo, et al., 2000, *Plant Cell*, 12: 677–690, "Resistance to Turnip Crinkle Virus in Arabidoipsis Is Regulated by Two Host Genes and Is Salicylic Acid Dependent but NPR1, Ethylene, and Jasmonate Independent".

Despres, et al., 2000, *Plant Cell*, 12: 279–290, "The Arabidopsis NPR1/NIMI Protein Enhances the DNA Binding Activity of a Subgroup of the TGA Family of bZIP Transcription Factors".

Lawton, et al., 1996, *Plant J.*, 10(1): 71–82, "Benzothiadiazole induces disease resistance in Arabidopsis by activation of the systemic acquired resistance signal transduction pathway".

Molina, et al., 1998, *Plant Cell*, 10: 1903–1914, "Impaired Fungicide Activity in Plants Blocked in Disease Resistance Signal Transduction".

Sanmiguel, P.J., et al., 1998, *EMBL Accession No. AF050451*, "*Zea mays* retrotransposon Opie–1 5'LTR, partial sequence".

Kadyrzhanova, D., et al., 1995, *EMBL Accession No. L43984*, "*Hordeum vulgare* (clone ABG377) chromosome 3H STS mRNA, sequence tagged site".

Shoemaker, R., et al., 1999, *EMBL Accession No. AI442277*, "sa66a04.y1 Gm–c1004 Glycine max cDNA clone Genome Systems Clone ID: Gm–c1004–4231 5' similar to TR:P93002 P93002 Regulatory Protein NPR1.; mRNA sequence".

* cited by examiner

SEQUENCE LISTING

```
<160> NUMBER OF SEQ ID NOS: 6

<210> SEQ ID NO 1
<211> LENGTH: 2154
<212> TYPE: DNA
<213> ORGANISM: Zea mays
<220> FEATURE:
<221> NAME/KEY: CDS
<222> LOCATION: (67)...(1929)
<221> NAME/KEY: 3'UTR
<222> LOCATION: (1933)...(2154)
<221> NAME/KEY: 5'UTR
<222> LOCATION: (1)...(66)

<400> SEQUENCE: 1
gtcgtagtgg tccgggtccg gcacaagtag gggctcgcgt cttgcgcttg gcagttgtgg      60 gaagcc atg gag ccg tcg tcg tcc atc acg ttc gcg tcg tcg tcg tcg     108
       Met Glu Pro Ser Ser Ser Ile Thr Phe Ala Ser Ser Ser Ser
```

```
       1                5                    10
tac ctg tcc aac ggc tcg agc ccc tgt tcc gtc gcg ctg ccg ccg cca    156
Tyr Leu Ser Asn Gly Ser Ser Pro Cys Ser Val Ala Leu Pro Pro Pro
 15              20                  25                  30 ggg ccg ccc cag act ccc ccg ttg cct gcc ggc cag ggg tgg ggt ggt    204
Gly Pro Pro Gln Thr Pro Pro Leu Pro Ala Gly Gln Gly Trp Gly Gly
             35                  40                  45 gga gtc gct gcc gca ggg agc gga ggc agc gtg gag gcc gtg agc ctg    252
Gly Val Ala Ala Ala Gly Ser Gly Gly Ser Val Glu Ala Val Ser Leu
                 50                  55                  60 aac cgg ctc agc aaa aac ctc gag cgg ctg ctc ctc gac ccg gac cta    300
Asn Arg Leu Ser Lys Asn Leu Glu Arg Leu Leu Leu Asp Pro Asp Leu
             65                  70                  75 gac tgc agc gac gcc gac gtc gat gtg ccc gac ggt ggg ccg ccc gta    348
Asp Cys Ser Asp Ala Asp Val Asp Val Pro Asp Gly Gly Pro Pro Val
         80                  85                  90 ccc atc cac cgc tgc atc ctt gcc gca cgc agc gac ttc ttc tac gac    396
Pro Ile His Arg Cys Ile Leu Ala Ala Arg Ser Asp Phe Phe Tyr Asp
 95                 100                 105                 110 ctc ttc gcc gct cgc ggc cgc gca ggg gca gcg cgc ggt gat gcg gcc    444
Leu Phe Ala Ala Arg Gly Arg Ala Gly Ala Ala Arg Gly Asp Ala Ala
                115                 120                 125 gcc ggc gcc gga gta gcc gcg gag ggg gct gcc agt gga agg ccg cgg    492
Ala Gly Ala Gly Val Ala Ala Glu Gly Ala Ala Ser Gly Arg Pro Arg
            130                 135                 140 tac aag atg gag gat ctc gtt ccc gcc ggc cgc gtg ggg cgc gag gcc    540
Tyr Lys Met Glu Asp Leu Val Pro Ala Gly Arg Val Gly Arg Glu Ala
        145                 150                 155 ttc cag gcg ttt ctg ggg tac ctg tac acc ggc aag ctc cgg ccg gca    588
Phe Gln Ala Phe Leu Gly Tyr Leu Tyr Thr Gly Lys Leu Arg Pro Ala
    160                 165                 170 ccg gtc gac gtg gtg tct tgt gct gac cca gtg tgc cat cac gat tcg    636
Pro Val Asp Val Val Ser Cys Ala Asp Pro Val Cys His His Asp Ser
175                 180                 185                 190 tgc ccg ccg gcc atc agg tcc gcg gtc gag ctc atg tac gcg gcg tgt    684
Cys Pro Pro Ala Ile Arg Ser Ala Val Glu Leu Met Tyr Ala Ala Cys
                195                 200                 205 acc ttc aag atc ccc gag ctc acc tcg ctc ttc cag cgc cgg ctt ctt    732
Thr Phe Lys Ile Pro Glu Leu Thr Ser Leu Phe Gln Arg Arg Leu Leu
            210                 215                 220 aat ttt gta gac aag act cta gtg gag gat gtt att cct att ctg gaa    780
Asn Phe Val Asp Lys Thr Leu Val Glu Asp Val Ile Pro Ile Leu Glu
        225                 230                 235 gtt gct tcc cac tca ggg ctg act caa gtg atc gac aaa tgt att caa    828
Val Ala Ser His Ser Gly Leu Thr Gln Val Ile Asp Lys Cys Ile Gln
    240                 245                 250 agg att gct aga tca gat ctc gac gat ata tct ttg gat aag gag ctc    876
Arg Ile Ala Arg Ser Asp Leu Asp Asp Ile Ser Leu Asp Lys Glu Leu
255                 260                 265                 270 cct cca gaa gca gtt gat gag ata aaa aat ttg cgc aag aag tca caa    924
Pro Pro Glu Ala Val Asp Glu Ile Lys Asn Leu Arg Lys Lys Ser Gln
                275                 280                 285 act gct gat ggt gat acg ttc att tcg gac cct gtg cat gag aaa aga    972
Thr Ala Asp Gly Asp Thr Phe Ile Ser Asp Pro Val His Glu Lys Arg
            290                 295                 300 gtc aga aga atc cac agg gca ctt gac tct gat gat gtt gag ctt gtg   1020
Val Arg Arg Ile His Arg Ala Leu Asp Ser Asp Asp Val Glu Leu Val
        305                 310                 315 aag ttg ctt ctt aat gag tcc gac atc aca tta gat gat gcc aac gca   1068
```

```
                                                          -continued

Lys Leu Leu Leu Asn Glu Ser Asp Ile Thr Leu Asp Asp Ala Asn Ala
320                 325                 330 tta cac tat gct gct tct tac tgt gat cct aaa gtt gtc tca gag ctg    1116
Leu His Tyr Ala Ala Ser Tyr Cys Asp Pro Lys Val Val Ser Glu Leu
335                 340                 345                 350 tta gat ttg gca atg gct aac tta aat ttg aag aat agc cgt ggg tac    1164
Leu Asp Leu Ala Met Ala Asn Leu Asn Leu Lys Asn Ser Arg Gly Tyr
                355                 360                 365 aca gca ctc cac ttg gct gct atg agg aga gaa cca gct ata atc atg    1212
Thr Ala Leu His Leu Ala Ala Met Arg Arg Glu Pro Ala Ile Ile Met
            370                 375                 380 tgt ctc ctt aac aaa ggg gca aat gtg tca caa ctg aca gct gat ggc    1260
Cys Leu Leu Asn Lys Gly Ala Asn Val Ser Gln Leu Thr Ala Asp Gly
        385                 390                 395 agg agc gca att ggt att tgt cgg agg tta aca aga gca aaa gac tac    1308
Arg Ser Ala Ile Gly Ile Cys Arg Arg Leu Thr Arg Ala Lys Asp Tyr
400                 405                 410 aat aca aag atg gag cag ggt caa gaa tca aat aaa gat agg ctg tgt    1356
Asn Thr Lys Met Glu Gln Gly Gln Glu Ser Asn Lys Asp Arg Leu Cys
415                 420                 425                 430 ata gat att cta gag agg gag atg atg cgg aat cct atg gcg gtg gaa    1404
Ile Asp Ile Leu Glu Arg Glu Met Met Arg Asn Pro Met Ala Val Glu
                435                 440                 445 gat gcc gtc acc tcg cct ttg ttg gca gat gat ctt cac atg aag ctt    1452
Asp Ala Val Thr Ser Pro Leu Leu Ala Asp Asp Leu His Met Lys Leu
            450                 455                 460 ctc tac ctg gaa aac aga gtt gca ttt gct aga ttg ttc ttt cct gct    1500
Leu Tyr Leu Glu Asn Arg Val Ala Phe Ala Arg Leu Phe Phe Pro Ala
        465                 470                 475 gaa gcc aag gtc gcc atg caa atc gca caa gca gac acc aca gaa gaa    1548
Glu Ala Lys Val Ala Met Gln Ile Ala Gln Ala Asp Thr Thr Glu Glu
480                 485                 490 ttc ggc ggt ata gtt gca gtt gca gca agc act tct ggt aaa ctg agg    1596
Phe Gly Gly Ile Val Ala Val Ala Ala Ser Thr Ser Gly Lys Leu Arg
495                 500                 505                 510 gag gtg gac ctt aat gag acg cca gtg aca caa aac aaa agg ctc cgt    1644
Glu Val Asp Leu Asn Glu Thr Pro Val Thr Gln Asn Lys Arg Leu Arg
                515                 520                 525 tca agg gta gat gca ctg atg aaa aca gtg gag ctg ggc cgt cgg tac    1692
Ser Arg Val Asp Ala Leu Met Lys Thr Val Glu Leu Gly Arg Arg Tyr
            530                 535                 540 ttc ccg aac tgc tcg cag gtg ctg gac aag ttc ctg gag gac gat ctg    1740
Phe Pro Asn Cys Ser Gln Val Leu Asp Lys Phe Leu Glu Asp Asp Leu
        545                 550                 555 ccg gaa ggt ctg gac cag ttc tac ctc cag agg ggc aca gcc gat gag    1788
Pro Glu Gly Leu Asp Gln Phe Tyr Leu Gln Arg Gly Thr Ala Asp Glu
560                 565                 570 cag aag gtg aag agg atg cgc ttc tgc gag ctg aaa gag gac gtg ctg    1836
Gln Lys Val Lys Arg Met Arg Phe Cys Glu Leu Lys Glu Asp Val Leu
575                 580                 585                 590 aag gcg ttt agc aag gac aag gcg gag ggc agc gtg ttc tcg ggc ctg    1884
Lys Ala Phe Ser Lys Asp Lys Ala Glu Gly Ser Val Phe Ser Gly Leu
                595                 600                 605 tcc tcg tcg tcg tcg tgc tcg ccg ccc cag aag tat gcc cag agg         1929
Ser Ser Ser Ser Ser Cys Ser Pro Pro Gln Lys Tyr Ala Gln Arg
            610                 615                 620 tgatcaaggc accagttttt gccgtatagt ttgttatcat ggtcttcgag acttggaccc   1989
ggacagcata tagggacatg tacacctgtg tatgtatagt gcttacaatt ggcgtaagta   2049
```

```
gaactatatg tatggaacat aaggaaacat ggcaggaaca ccgtgcaaaa agatgaaaag    2109
atggccgaag tgctctatgc gaaaaaaaaa aaaaaaaaaa aaaaa                   2154
```

<210> SEQ ID NO 2
<211> LENGTH: 621
<212> TYPE: PRT
<213> ORGANISM: Zea mays

<400> SEQUENCE: 2

```
Met Glu Pro Ser Ser Ser Ile Thr Phe Ala Ser Ser Ser Ser Tyr Leu
 1               5                  10                  15

Ser Asn Gly Ser Ser Pro Cys Ser Val Ala Leu Pro Pro Gly Pro
            20                  25                  30

Pro Gln Thr Pro Pro Leu Pro Ala Gly Gln Gly Trp Gly Gly Val
        35                  40                  45

Ala Ala Ala Gly Ser Gly Gly Ser Val Glu Ala Val Ser Leu Asn Arg
 50                  55                  60

Leu Ser Lys Asn Leu Glu Arg Leu Leu Leu Asp Pro Asp Leu Asp Cys
 65                  70                  75                  80

Ser Asp Ala Asp Val Asp Val Pro Asp Gly Pro Pro Val Pro Ile
                85                  90                  95

His Arg Cys Ile Leu Ala Ala Arg Ser Asp Phe Phe Tyr Asp Leu Phe
                100                 105                 110

Ala Ala Arg Gly Arg Ala Gly Ala Ala Arg Gly Asp Ala Ala Ala Gly
            115                 120                 125

Ala Gly Val Ala Ala Glu Gly Ala Ala Ser Gly Arg Pro Arg Tyr Lys
        130                 135                 140

Met Glu Asp Leu Val Pro Ala Gly Arg Val Gly Arg Glu Ala Phe Gln
145                 150                 155                 160

Ala Phe Leu Gly Tyr Leu Tyr Thr Gly Lys Leu Arg Pro Ala Pro Val
                165                 170                 175

Asp Val Val Ser Cys Ala Asp Pro Val Cys His His Asp Ser Cys Pro
            180                 185                 190

Pro Ala Ile Arg Ser Ala Val Glu Leu Met Tyr Ala Ala Cys Thr Phe
        195                 200                 205

Lys Ile Pro Glu Leu Thr Ser Leu Phe Gln Arg Arg Leu Leu Asn Phe
    210                 215                 220

Val Asp Lys Thr Leu Val Glu Asp Val Ile Pro Ile Leu Glu Val Ala
225                 230                 235                 240

Ser His Ser Gly Leu Thr Gln Val Ile Asp Lys Cys Ile Gln Arg Ile
                245                 250                 255

Ala Arg Ser Asp Leu Asp Asp Ile Ser Leu Asp Lys Glu Leu Pro Pro
            260                 265                 270

Glu Ala Val Asp Glu Ile Lys Asn Leu Arg Lys Ser Gln Thr Ala
        275                 280                 285

Asp Gly Asp Thr Phe Ile Ser Asp Pro Val His Glu Lys Arg Val Arg
    290                 295                 300

Arg Ile His Arg Ala Leu Asp Ser Asp Val Glu Leu Val Lys Leu
305                 310                 315                 320

Leu Leu Asn Glu Ser Asp Ile Thr Leu Asp Ala Asn Ala Leu His
                325                 330                 335

Tyr Ala Ala Ser Tyr Cys Asp Pro Lys Val Val Ser Glu Leu Leu Asp
            340                 345                 350

Leu Ala Met Ala Asn Leu Asn Leu Lys Asn Ser Arg Gly Tyr Thr Ala
```

```
                355                 360                 365
Leu His Leu Ala Ala Met Arg Arg Glu Pro Ala Ile Ile Met Cys Leu
        370                 375                 380
Leu Asn Lys Gly Ala Asn Val Ser Gln Leu Thr Ala Asp Gly Arg Ser
385                 390                 395                 400
Ala Ile Gly Ile Cys Arg Arg Leu Thr Arg Ala Lys Asp Tyr Asn Thr
                405                 410                 415
Lys Met Glu Gln Gly Gln Glu Ser Asn Lys Asp Arg Leu Cys Ile Asp
                420                 425                 430
Ile Leu Glu Arg Glu Met Met Arg Asn Pro Met Ala Val Glu Asp Ala
            435                 440                 445
Val Thr Ser Pro Leu Leu Ala Asp Asp Leu His Met Lys Leu Leu Tyr
    450                 455                 460
Leu Glu Asn Arg Val Ala Phe Ala Arg Leu Phe Phe Pro Ala Glu Ala
465                 470                 475                 480
Lys Val Ala Met Gln Ile Ala Gln Ala Asp Thr Thr Glu Glu Phe Gly
                485                 490                 495
Gly Ile Val Ala Val Ala Ala Ser Thr Ser Gly Lys Leu Arg Glu Val
                500                 505                 510
Asp Leu Asn Glu Thr Pro Val Thr Gln Asn Lys Arg Leu Arg Ser Arg
            515                 520                 525
Val Asp Ala Leu Met Lys Thr Val Glu Leu Gly Arg Arg Tyr Phe Pro
530                 535                 540
Asn Cys Ser Gln Val Leu Asp Lys Phe Leu Glu Asp Leu Pro Glu
545                 550                 555                 560
Gly Leu Asp Gln Phe Tyr Leu Gln Arg Gly Thr Ala Asp Glu Gln Lys
                565                 570                 575
Val Lys Arg Met Arg Phe Cys Glu Leu Lys Glu Asp Val Leu Lys Ala
                580                 585                 590
Phe Ser Lys Asp Lys Ala Glu Gly Ser Val Phe Ser Gly Leu Ser Ser
            595                 600                 605
Ser Ser Ser Cys Ser Pro Pro Gln Lys Tyr Ala Gln Arg
    610

<210> SEQ ID NO 3
<211> LENGTH: 7789
<212> TYPE: DNA
<213> ORGANISM: Zea mays
<220> FEATURE:
<221> NAME/KEY: promoter
<222> LOCATION: (1)...(2715)
<221> NAME/KEY: 5'UTR
<222> LOCATION: (2716)...(2781)
<221> NAME/KEY: exon
<222> LOCATION: (2782)...(3435)
<221> NAME/KEY: intron
<222> LOCATION: (3436)...(3987)
<221> NAME/KEY: exon
<222> LOCATION: (3988)...(4738)
<221> NAME/KEY: intron
<222> LOCATION: (4739)...(5274)
<221> NAME/KEY: exon
<222> LOCATION: (5275)...(5475)
<221> NAME/KEY: intron
<222> LOCATION: (5476)...(5665)
<221> NAME/KEY: exon
<222> LOCATION: (5666)...(5922)
<221> NAME/KEY: 3'UTR
<222> LOCATION: (5926)...(6124)

<400> SEQUENCE: 3
```

-continued

| | |
|---|---|
| gcggccgcgt aatacgactc actatagggc gaagaattcg gatctccttc cttatttggc | 60 |
| gaagccgacc gttggcgctt tggagccgtt ggcgcaccgg acactgtccg gtgcacaccg | 120 |
| gacagtcagg tgccccttc cgaccgttgg ctcggccacg tgtttcgcgc ggatcgcgcg | 180 |
| gcagaccgtt ggcccgaccg accgttggct caccggacag tccggtgcac accagacagt | 240 |
| ccggtgaatt atagccgtac gccgttaatc acttcccgag agcagcaagt tcgcctgagc | 300 |
| cagcctggcg caccggacac tgtccggtga accaccggac agtccggtgc acccagtcag | 360 |
| agctgacttt ggctgaacaa agtcatcttt agttccaact tgattttcc tgtttccagc | 420 |
| acttagacac aatacattag tctctaaaac aatgtattaa ttctgagaaa catacccttta | 480 |
| tacttggttt gtactttgtc caccatttaa cacttgggca cttgtgttgg acactaaatc | 540 |
| accaaaatac ttagaaatgg cccaagggca catttccctt tcaacagtcc ggtgccacac | 600 |
| cggacagtcc ggtgacctct gacttctgtg ttctaacttc tgtcgcggca ctgtttcgca | 660 |
| ctatagcgtt ttgcagtcga ccgttggcgc acagagagcc attgctccgc tggctgaccg | 720 |
| gacagtccga tgaattatag cggascgcgc tctgaattc ccgagtgtgg cctgtttgaa | 780 |
| gggcgcctgg cctggtgcac cgaacaatgt atggtgcgcc aaaaatcagc acactcaagt | 840 |
| cctttgcttc atttttatt gtgtcgctaa ctggatttct ttttggtttg tgttgaacct | 900 |
| tatgcacctg agataaatca catctagcca aactagttag tccatgtggt ttgtgttgat | 960 |
| cgtcaactac taaaatctat ttatagaaag tggttaaccc tatttcccctt tcagcacact | 1020 |
| ctatatagtg cttgagacct cgacatgaag gtgtcctagg aagccaaggc tctcgcgtaa | 1080 |
| ggtcctcgac atgcaggacc ctaggccccg ttagaatggg gcttgtccat aagagagttg | 1140 |
| ggctctaaga tgcatgactg acactgtgcg tctgtcgttt cttaataaag ttatagatga | 1200 |
| tgttttgcca acatctgatg atatgtcttg gtgcttacaa agccttgtt ttttatcttc | 1260 |
| ctttcgtctt aataaagatc catattacat ttatatttac tatgtcatat atataccctca | 1320 |
| ctatctcgaa gatacatctc gttgcggaag cataaggtag ctttggaggt aaagcttaga | 1380 |
| gcgacatgtg ggtgcaacaa acaaacatgg gggcacaaca cacctcacct catataacta | 1440 |
| atttggcttg caaatcgaga gtcccgtacg aaaagtactc gttgtctctt gacccaataa | 1500 |
| atcaaataca ccttcttaca caatttgtcc attttatatt tttcgtttcc aataacaaac | 1560 |
| tcaaagtgac ttgtttttt ggacctttga cacatagcct ttaaagtaga tttcacaatt | 1620 |
| taagcttgtt atgtaaaaca aactaatttc gagagaggc gattgaggag aaagtctgcg | 1680 |
| gtcgatgatt caattggacg aaatcgatgt ttaaactgtc ttgttgatta aatttctagc | 1740 |
| ttcacacgtg cttgaacggc gtaggaagtg ttggaatttc ccttcttatg atttattaga | 1800 |
| gtagagtttt gttacagttt atttacggat tcattacggt atttattagg gatacgttga | 1860 |
| catataactt cagtctttct ttttaatag tcacaagaaa ctttcacaca cctactagga | 1920 |
| gtaacagaaa aacatggaca tattgatttt tgaaaaaga aatattgaca gataaggtgt | 1980 |
| tgggaccgt agagactaga gaggatgagg acgacgccag gcagacgagc cttgccgatt | 2040 |
| gccgtcgacg tcaccctggt caggcgtcac ttgacgacgt atacaggggc acagggctca | 2100 |
| ggttttcctt caaattgcgc cgaaatactc gagatttctt ggatttttt acttgtttat | 2160 |
| tctattctcc ttccggcgcc tctctagtct attctccttc ctcgtcgagt cgtcgtcttc | 2220 |
| ttcgatccac tctttcccc atccctatct ccctactttc cacgcaactg cgtttccccc | 2280 |
| ggactcttct tccacgattc cgttggaccc ctaccgctcc tcagtcagtc ctcgcccctc | 2340 |
| ccagcaccgg ccaacaatcc ctcacgttat tccctgtagc tactatgctg ccctcttgga | 2400 |

-continued

```
tccctttttc acttgtctga gatttagcca ccgcccggta ggaagaagaa ggggaagcac    2460
catattttct gttcctggcc tgacgcagcg ccggtgagat ttcagtccgg gatcggcaac    2520
gctgggagga ctcgcgtgtg atttacgccg acttccgtgc cgctctagga agggtcacgt    2580
cgaggaggct tttgccgacg cggatttgcc tggagccagc caagcagagc gcagaattgg    2640
gggtgtttgg ccgtgcaaag ccagaaagtt ctcggtttgg ctgccgaaac cgcttgaggc    2700
gaccaccatc tcatggtcgt agtggtccgg gtccggcaca agtaggggct cgcgtcttgc    2760
gcttggcagt tgtgggaagc catggagccg tcgtcgtcca tcacgttcgc gtcgtcgtcg    2820
tcgtacctgt ccaacggctc gagcccctgt tccgtcgcgc tgccgccgcc agggccgccc    2880
cagactcccc cgttgcctgc cggccagggg tggggtggtg gagtcgctgc cgcagggagc    2940
ggaggcagcg tggaggccgt gagcctgaac cggctcagca aaaacctcga gcggctgctc    3000
ctcgacccga acctagactg cagcgacgcc gacgtcgatg tgcccgacgg tgggccgccc    3060
gtacccatcc accgctgcat ccttgccgca cgcagcgact tcttctacga cctcttcgcc    3120
gctcgcggcc gcgcagggc agcgcgcggt gatgcggccg ccggcgccgg agtagccgcg    3180 gaggggctg ccagtggaag gccgcggtac aagatggagg atctcgttcc cgccggccgc    3240
gtggggcgcg aggccttcca ggcgtttctg gggtacctgt acaccggcaa gctccggccg    3300
gcaccggtcg acgtggtgtc ttgtgctgac ccagtgtgcc atcacgattc gtgcccgccg    3360
gccatcaggt ccgcggtcga gctcatgtac gcggcgtgta ccttcaagat ccccgagctc    3420
acctcgctct tccaggtgag acgcaatttg gttcttgctc gccccattgt caataggatt    3480
aaactctaat ttctttagga attgtttcgt tctatgccaa tactgtacat ggcttcggta    3540
gactagaaat ggatttgtga tttttttct ccaatccgag tgttgactac atcactacaa    3600
aaagctatca atagctgaac tgctaaaatt gctgattttg ttttctccaa tccgagtgtt    3660
gaccacatca ctgcaaaaag ttattaatag ctgaatcgct acaattgttc aattgttgat    3720 tttgttttt ccaatccgag tggtgacact acaaaaaact attaatagtt gaactactaa    3780
aattgttggc tattgctttt ttagttgatt caagcgaacc tggtggcttg aagtctatga    3840
attgaaatgg aatcattatt cattaggctg ctcaacattt gtatattaca tttatggctg    3900
tataatttat caatctgttt aacatcaatt cagctttgct ttgtcgattt atggaaggca    3960
aatggttaac atggtcttct tctacagcgc cggcttctta attttgtaga caagactcta    4020
gtggaggatg ttattcctat tctggaagtt gcttcccact cagggctgac tcaagtgatc    4080
gacaaatgta ttcaaaggat tgctagatca gatctcgacg atatatcttt ggataaggag    4140
ctccctccag aagcagttga tgagataaaa aatttgcgca agaagtcaca aactgctgat    4200
ggtgatacgt tcatttcgga ccctgtgcat gagaaaagag tcagaagaat ccacagggca    4260
cttgactctg atgatgttga gcttgtgaag ttgcttctta atgagtccga catcacatta    4320
gatgatgcca acgcattaca ctatgctgct tcttactgtg atcctaaagt tgtctcagag    4380
ctgttagatt tggcaatggc taacttaaat ttgaagaata gccgtgggta cacagcactc    4440
cacttggctg ctatgaggag agaaccagct ataatcatgt gtctccttaa caaggggca    4500 aatgtgtcac aactgacagc tgatggcagg agcgcaattg gtatttgtcg gaggttaaca    4560
agagcaaaag actacaatac aaagatggag cagggtcaag aatcaaataa agataggctg    4620
tgtatagata ttctagagag ggagatgatg cggaatccta tggcggtgga agatgccgtc    4680
acctcgcctt tgttggcaga tgatcttcac atgaagcttc tctacctgga aaacagaggt    4740
```

-continued

```
gaagtccata ccatgcttga tagaatggct ctgattggtt gcctgttgcc gcttcaaatt    4800
ttgaaaattt aaaagcttgg aggtcaggtg gattgattca ggctagcttg tagactaatg    4860
acatgtgcct gacctttgt tctcataaag agggaaaaag gaaaacgccc accccatacc    4920
acatcaattt ctcctttttt tcaaattggt gaaagctgta catgttgtag gaaataaaca    4980
attgtagtca caaagcccaa attaatctaa ttacagatga caagcctgga ttattaaatt    5040
gccacttgcc tgtccatatt gcacacaacc tagtagtgtc ctagttctag ataatataac    5100
gagaatgatt tcacaccact ggatgatgat caaatagcac cttagaactt ggggttggga    5160
tatgtcattg tcgtgagctt tgtcttatgt tcacgtttat aagaagattg tgatttatgt    5220
tattggctac attattttcc ctgcaccata acattctaag tattgttcct gcagttgcat    5280
ttgctagatt gttctttcct gctgaagcca aggtcgccat gcaaatcgca caagcagaca    5340
ccacagaaga attcggcggt atagttcag ttgcagcaag cacttctggt aaactgaggg    5400
aggtggacct taatgagacg ccagtgacac aaaacaaaag gctccgttca agggtagatg    5460
cactgatgaa aacaggtgaa agtttcaacc gtcaaccttt tccattgtag tgaacatgcc    5520
ctgcagctat ctccagaaaa tttagttcgg acgcaatcac ggattctacg tgtacctgaa    5580
gtattgtgac tatgttcaaa atacatgatt gatacaatgt atctgatctg gtgttcgccc    5640
atttttatcc gatgacttct tgcagtggag ctgggccgtc ggtacttccc gaactgctcg    5700
caggtgctgg acaagttcct ggaggacgat ctgccggaag gtctggacca gttctacctc    5760 cagagggca cagccgatga gcagaaggtg aagaggatgc gcttctgcga gctgaaagag    5820
gacgtgctga aggcgtttag caaggacaag gcggagggca gcgtgttctc gggcctgtcc    5880
tcgtcgtcgt cgtgctcgcc gccccagaag tatgcccaga ggtgatcaag gcaccagttt    5940
ttgccgtata gtttgttatc atggtcttcg agacttggac ccggacagca tagggaca    6000 tgtacacctg tgtatgtata gtgcttacaa ttggcgtaag tagaactata tgtatggaac    6060
ataaggaaac atggcaggaa caccgtgcaa aaagatgaaa agatggccga agtgctctat    6120
gcgagtgccc acctgattcg atggcccctat tcaacgcgcgc cctgtcagca tgctgcatgc    6180
ccactgagac cttcggttgc atagggatag gaggagattt ctgttcaatt ttggctagca    6240
agtgatatag gggtgtttag gactgtttca ctttatgaaa atcaacttag ctcataaaca    6300
cttttaactt caataactta ggtcctgttt ggagtggctg tatttttcta gtcccaagaa    6360
aataatgtgg tatctgagaa taccatggtc tagaaaccaa aatgtgtttg gcagactctt    6420
ttaaaccatg gtatttaaaa tcttggtttt gacaagacca cattatttct gggtatagaa    6480
tactgtccag actagggctg gaaatgagcc gagttcggct cggctcggtg cggctcgttg    6540
actgaacgag ctcgactcgg ctcgtccatt ccacgagctg gtgaaagagg ctcggctcgg    6600
ctcgacctta gctcgcgagc catattcttg tacttatcgt ttcattattt gatgaattaa    6660
cattatataa atttgaaata taaatcatc attctacatt atgagtaaat taaactataa    6720
cttgtaatat attcatcatc aaagactaaa aaataagcta ttatccataa aattatctaa    6780
tatttattat tattccataa attgatcatt tttgcaaggc tcgtgagctg gaacgagccg    6840
gctcggctcg gctcgctgca aaaacgagct cgaagaaggg gctcggcttg gctcgttcga    6900
ggctcgcgag ctgcgccgag ccgagccgct ccgagctcga gccggctcgc gagcctcgag    6960
ctaattttcc agccctagtc cagaccaaag tttttcgtca gagcgcgcga agcgacccta    7020
atgtccgcgc ccttttctca ccgtccacgc atctcttccc ctcaattcta aggctttctc    7080
caacaagaaa cgttaaagcg ttcggtacgc tatatttagc gtgtaccttc gtctccaaca    7140
```

```
agcacatgta tagcgttcgc taaaatttag cggagcctca gcgtccgcca aatctagcat   7200
ctcctgtccg tccgctattc tgtcagctct cgtacgggaa gccgtatgct actatcatag   7260
cgccaataaa aaacaaacaa tgccaggaac gtctccgctg accagtaaaa aagaactaaa   7320
aatggaacta aaagatcttc tatggacata tgtgagaacg accatttcat atattcaaca   7380
tcttttagct gtacataaat attttactat gtattctaca ataatttgta atttgttgaa   7440
aaatatgatt gcaataaatt atgttaatat ggttgccaaa atatatacga tgagatatag   7500
aacaaacatt gtagtttatg gattatgtta acactgtaga tatagagatt cgaatttagg   7560
tgacgttgct gaagatgaag aagatataga gaacataatc ttttagagaa tgctgtaaag   7620
gacagagaat atttctttag agaacggaat ttagggtacg ttgctggaga cagcctaata   7680
cagacactct tttcctcttt ctccattccc catcgcaaaa ctgggaggac ctagcttcgc   7740
cgcagatgtc gtcggtcccg ggacgctgat ctcgcctcag attccgtgg               7789
```

<210> SEQ ID NO 4
<211> LENGTH: 621
<212> TYPE: PRT
<213> ORGANISM: Zea mays

<400> SEQUENCE: 4

```
Met Glu Pro Ser Ser Ile Thr Phe Ala Ser Ser Ser Ser Tyr Leu
1               5                   10                  15

Ser Asn Gly Ser Ser Pro Cys Ser Val Ala Leu Pro Pro Gly Pro
                20                  25                  30

Pro Gln Thr Pro Pro Leu Pro Ala Gly Gln Gly Trp Gly Gly Val
            35                  40                  45

Ala Ala Gly Ser Gly Gly Ser Val Glu Ala Val Ser Leu Asn Arg
        50                  55                  60

Leu Ser Lys Asn Leu Glu Arg Leu Leu Leu Asp Pro Asp Leu Asp Cys
65                  70                  75                  80

Ser Asp Ala Asp Val Asp Val Pro Asp Gly Gly Pro Pro Val Pro Ile
                85                  90                  95

His Arg Cys Ile Leu Ala Ala Arg Ser Asp Phe Phe Tyr Asp Leu Phe
            100                 105                 110

Ala Ala Arg Gly Arg Ala Gly Ala Ala Arg Gly Asp Ala Ala Ala Gly
        115                 120                 125

Ala Gly Val Ala Ala Glu Gly Ala Ala Ser Gly Arg Pro Arg Tyr Lys
    130                 135                 140

Met Glu Asp Leu Val Pro Ala Gly Arg Val Gly Arg Glu Ala Phe Gln
145                 150                 155                 160

Ala Phe Leu Gly Tyr Leu Tyr Thr Gly Lys Leu Arg Pro Ala Pro Val
                165                 170                 175

Asp Val Val Ser Cys Ala Asp Pro Val Cys His His Asp Ser Cys Pro
            180                 185                 190

Pro Ala Ile Arg Ser Ala Val Glu Leu Met Tyr Ala Ala Cys Thr Phe
        195                 200                 205

Lys Ile Pro Glu Leu Thr Ser Leu Phe Gln Arg Arg Leu Leu Asn Phe
    210                 215                 220

Val Asp Lys Thr Leu Val Glu Asp Val Ile Pro Ile Leu Glu Val Ala
225                 230                 235                 240

Ser His Ser Gly Leu Thr Gln Val Ile Asp Lys Cys Ile Gln Arg Ile
                245                 250                 255
```

```
Ala Arg Ser Asp Leu Asp Asp Ile Ser Leu Asp Lys Glu Leu Pro Pro
            260                 265                 270

Glu Ala Val Asp Glu Ile Lys Asn Leu Arg Lys Lys Ser Gln Thr Ala
        275                 280                 285

Asp Gly Asp Thr Phe Ile Ser Asp Pro Val His Glu Lys Arg Val Arg
    290                 295                 300

Arg Ile His Arg Ala Leu Asp Ser Asp Val Glu Leu Val Lys Leu
305                 310                 315                 320

Leu Leu Asn Glu Ser Asp Ile Thr Leu Asp Asp Ala Asn Ala Leu His
                325                 330                 335

Tyr Ala Ala Ser Tyr Cys Asp Pro Lys Val Val Ser Glu Leu Leu Asp
            340                 345                 350

Leu Ala Met Ala Asn Leu Asn Leu Lys Asn Ser Arg Gly Tyr Thr Ala
        355                 360                 365

Leu His Leu Ala Ala Met Arg Arg Glu Pro Ala Ile Ile Met Cys Leu
    370                 375                 380

Leu Asn Lys Gly Ala Asn Val Ser Gln Leu Thr Ala Asp Gly Arg Ser
385                 390                 395                 400

Ala Ile Gly Ile Cys Arg Arg Leu Thr Arg Ala Lys Asp Tyr Asn Thr
                405                 410                 415

Lys Met Glu Gln Gly Gln Glu Ser Asn Lys Asp Arg Leu Cys Ile Asp
            420                 425                 430

Ile Leu Glu Arg Glu Met Met Arg Asn Pro Met Ala Val Glu Asp Ala
        435                 440                 445

Val Thr Ser Pro Leu Leu Ala Asp Asp Leu His Met Lys Leu Leu Tyr
    450                 455                 460

Leu Glu Asn Arg Val Ala Phe Ala Arg Leu Phe Phe Pro Ala Glu Ala
465                 470                 475                 480

Lys Val Ala Met Gln Ile Ala Gln Ala Asp Thr Thr Glu Glu Phe Gly
                485                 490                 495

Gly Ile Val Ala Val Ala Ala Ser Thr Ser Gly Lys Leu Arg Glu Val
            500                 505                 510

Asp Leu Asn Glu Thr Pro Val Thr Gln Asn Lys Arg Leu Arg Ser Arg
        515                 520                 525

Val Asp Ala Leu Met Lys Thr Val Glu Leu Gly Arg Arg Tyr Phe Pro
    530                 535                 540

Asn Cys Ser Gln Val Leu Asp Lys Phe Leu Glu Asp Leu Pro Glu
545                 550                 555                 560

Gly Leu Asp Gln Phe Tyr Leu Gln Arg Gly Thr Ala Asp Glu Gln Lys
                565                 570                 575

Val Lys Arg Met Arg Phe Cys Glu Leu Lys Glu Asp Val Leu Lys Ala
            580                 585                 590

Phe Ser Lys Asp Lys Ala Glu Gly Ser Val Phe Ser Gly Leu Ser Ser
        595                 600                 605

Ser Ser Ser Cys Ser Pro Pro Gln Lys Tyr Ala Gln Arg
    610

<210> SEQ ID NO 5
<211> LENGTH: 2715
<212> TYPE: DNA
<213> ORGANISM: Zea mays
<220> FEATURE:
<221> NAME/KEY: promoter
<222> LOCATION: (1)...(2715)

<400> SEQUENCE: 5
```

-continued

```
gcggccgcgt aatacgactc actatagggc gaagaattcg gatctccttc cttatttggc      60
gaagccgacc gttggcgctt tggagccgtt ggcgcaccgg acactgtccg gtgcacaccg     120
gacagtcagg tgcccccttc cgaccgttgg ctcggccacg tgtttcgcgc ggatcgcgcg     180
gcagaccgtt ggcccgaccg accgttggct caccggacag tccggtgcac accagacagt     240
ccggtgaatt atagccgtac gccgttaatc acttcccgag agcagcaagt tcgcctgagc     300
cagcctggcg caccgacac tgtccggtga accaccggac agtccggtgc acccagtcag     360
agctgacttt ggctgaacaa agtcatcttt agttccaact tgattttttcc tgtttccagc    420
acttagacac aatacattag tctctaaaac aatgtattaa ttctgagaaa catacccttta   480
tacttggttt gtactttgtc caccatttaa cacttgggca cttgtgttgg acactaaatc     540
accaaaatac ttagaaatgg cccaagggca catttccctt tcaacagtcc ggtgccacac     600
cggacagtcc ggtgacctct gacttctgtg ttctaacttc gtcgcggca ctgtttcgca      660
ctatagcgtt ttgcagtcga ccgttggcgc acagagagcc attgctccgc tggctgaccg     720
gacagtccga tgaattatag cggascgcgc tctgaattc ccgagtgtgg cctgtttgaa      780
gggcgcctgg cctggtgcac cgaacaatgt atggtgcgcc aaaaatcagc acactcaagt     840
cctttgcttc attttttatt gtgtcgctaa ctggatttct ttttggtttg tgttgaacct     900
tatgcacctg agataaatca catctagcca aactagttag tccatgtggt ttgtgttgat     960
cgtcaactac taaaatctat ttatagaaag tggttaaccc tatttccctt tcagcacact    1020
ctatatagtg cttgagacct cgacatgaag gtgtcctagg aagccaaggc tctcgcgtaa    1080
ggtcctcgac atgcaggacc ctaggccccg ttagaatggg gcttgtccat aagagagttg    1140
ggctctaaga tgcatgactg acactgtgcg tctgtcgttt cttaataaag ttatagatga    1200
tgttttgcca acatctgatg atatgtcttg gtgcttacaa aagccttgtt ttttatcttc    1260
ctttcgtctt aataaagatc catattacat ttatatttac tatgtcatat atatacctca    1320
ctatctcgaa gatacatctc gttgcggaag cataaggtag cttttggaggt aaagcttaga   1380
gcgacatgtg ggtgcaacaa acaaacatgg gggcacaaca cacctcacct catataacta    1440
atttggcttg caaatcgaga gtcccgtacg aaaagtactc gttgtctctt gacccaataa    1500
atcaaataca ccttcttaca caatttgtcc attttatatt tttcgtttcc aataacaaac    1560
tcaaagtgac ttgtttttttt ggacctttga cacatagcct ttaaagtaga tttcacaatt   1620
taagcttgtt atgtaaaaca aactaatttc gagagaggct gattgaggag aaagtctgcg    1680
gtcgatgatt caattggacg aaatcgatgt ttaaactgtc ttgttgatta aatttctagc    1740
ttcacacgtg cttgaacggc gtaggaagtg ttggaatttc ccttcttatg atttattaga    1800
gtagagtttt gttacagttt atttacggat tcattacggt atttattagg gatacgttga    1860
catataactt cagtctttct tttttaatag tcacaagaaa ctttcacaca cctactagga    1920
gtaacagaaa aacatggaca tattgatttt tgaaaaaga aatattgaca gataaggtgt     1980
tgggaccgt agagactaga gaggatgagg acgacgccag gcagacgagc cttgccgatt     2040
gccgtcgacg tcaccctggt caggcgtcac ttgacgacgt atacagggc acagggctca     2100
ggttttcctt caaattgcgc cgaaatactc gagatttctt ggatttttt acttgtttat     2160
tctattctcc ttccggcgcc tctctagtct attctccttc ctcgtcgagt cgtcgtcttc    2220
ttcgatccac tctttccccc atccctatct ccctactttc cacgcaactg cgtttccccc    2280
ggactcttct tccacgattc cgttggaccc ctaccgctcc tcagtcagtc ctcgcccctc    2340
```

-continued

```
ccagcaccgg ccaacaatcc ctcacgttat tccctgtagc tactatgctg ccctcttgga      2400
tccctttttc acttgtctga gatttagcca ccgcccggta ggaagaagaa ggggaagcac      2460
catattttct gttcctggcc tgacgcagcg ccggtgagat ttcagtccgg gatcggcaac      2520
gctgggagga ctcgcgtgtg atttacgccg acttccgtgc cgctctagga agggtcacgt      2580
cgaggaggct tttgccgacg cggatttgcc tggagccagc caagcagagc gcagaattgg      2640
gggtgtttgg ccgtgcaaag ccagaaagtt ctcggtttgg ctgccgaaac cgcttgaggc      2700
gaccaccatc tcatg                                                      2715

<210> SEQ ID NO 6
<211> LENGTH: 36
<212> TYPE: DNA
<213> ORGANISM: Artificial Sequence
<220> FEATURE:
<223> OTHER INFORMATION: Designed oligonucleotide based upon an adaptor
      used for cDNA library construction and poly(dT) to
      remove clones which have a poly(A) tail but no
      cDNA insert.

<400> SEQUENCE: 6
tcgacccacg cgtccgaaaa aaaaaaaaaa aaaaaa                                 36
```

MAIZE NPR1 PROMOTER AND METHODS OF USE IN PLANT GENE EXPRESSION

CROSS-REFERENCE TO RELATED APPLICATIONS

This application is a divisional of and claims priority to and benefit of copending U.S. application Ser. No. 09/551,778, filed Apr. 18, 2000, now U.S. Pat. No. 6,504,084, which claims priority to and benefit of U.S. Provisional Application Serial No. 60/130,692, filed Apr. 23, 1999, both of which are herein incorporated by reference.

TECHNICAL FIELD

The present invention relates generally to plant molecular biology. More specifically, it relates to nucleic acids and methods for modulating their expression in plants and to transforming genes that enhance disease resistance.

BACKGROUND OF THE INVENTION

Disease in plants is produced by biotic and abiotic causes. Biotic causes include fungi, viruses, insects, bacteria, and nematodes. Of these, fungi are the most frequent causative agents of disease in plants. Abiotic causes of disease in plants include extremes of temperature, water, oxygen, soil pH, plus nutrient-element deficiencies and imbalances, excess heavy metals, and air pollution.

Plant disease outbreaks have resulted in catastrophic crop failures that have triggered famines and caused major social change. Generally, the best strategy for plant disease control is to use resistant cultivars selected or developed by plant breeders for this purpose. However, the potential for serious crop disease epidemics persists today, as evidenced by outbreaks of the Victoria blight of oats and southern corn leaf blight. Accordingly, molecular methods are needed to supplement traditional breeding methods to protect plants from pathogen attack.

A host of cellular processes enables plants to defend themselves from disease caused by pathogenic agents. These processes apparently form an integrated set of resistance mechanisms that is activated by initial infection and then limits further spread of the invading pathogenic microorganism.

After recognition of a potentially pathogenic microbe, plants can activate an array of biochemical responses. Generally, the plant responds by inducing several local responses in the cells immediately surrounding the infection site. The most common resistance response observed in both nonhost and race-specific interactions is termed the "hypersensitive response" (HR). In the hypersensitive response, cells contacted by the pathogen, and often neighboring cells, rapidly collapse and dry producing a necrotic fleck. Other responses include the deposition of callose, the physical thickening of cell walls by lignification, and the synthesis of various antibiotic small molecules and proteins. Genetic factors in both the host and the pathogen determine the specificity of these local responses, which can be very effective in limiting the spread of infection.

In many plant species, an initial inoculation by a necrotizing pathogen can immunize the plant to subsequent infection. Particularly well characterized examples of plant immunity are the phenomenon of systemic acquired resistance (SAR) and induced resistance. In these systems, inoculation by a necrotizing pathogen results in systemic protection against subsequent infections by that pathogen as well as a number of other agronomically important bacterial, fungal and viral pathogens. Systemic acquired resistance can also be triggered by chemical immunization.

SAR is characterized by the expression of SAR genes, including pathogenesis-related (PR) genes. The SAR genes are induced following infection by a pathogen. Some of these genes have a role in providing systemic acquired resistance to the plant. The resulting proteins are believed to be a common defensive systemic response of plants to infection by pathogens. When the SAR signal transduction pathway is blocked, plants become more susceptible to pathogens that normally cause disease, and they become susceptible to some infectious agents that would not normally cause disease. Salicylic acid (SA) accumulation appears to be required for SAR signal transduction.

A gene in Arabidopsis identified as NPR1 or NIM1 has recently been found which controls the onset of SAR (Cao, et al., *Cell*, 88:57–63 (1997); WO 97/49822; and WO 98/826082, all of which are herein incorporated by reference). A mutation in the NPR1 gene (nim1/sai1) results in enhanced disease susceptibility (Cao, et al., *The Plant Cell*, 6:1583–1592 (1994); Volko, et al., *Genetics*, 149:537–548; Shah, et al., *MPMI*, 10(1):69–78 (1997); and Delaney, et al., *Proc. Natl. Acad. Sci. USA*, 92:6602–6606 (1995)). By overexpression of the NPR1 gene in Arabidopsis a battery of downstream pathogenesis-related genes are induced (Cao, et al., *Proc. Natl. Acad. Sci. USA*, 95:6531–6536 (1998). This overexpression of NPR1 conferred resistance to the pathogens *Pseudomonas syringae* and *Peronospora parasitica* with no obvious detrimental effects on the plants.

Expression of heterologous DNA sequence in a plant host is dependent upon the presence of an operably linked promoter that is functional within the plant host. Choice of the promoter sequence will determine when and where within the organism the heterologous DNA sequence is expressed. Thus, where continuous expression is desired throughout the cells of a plant, constitutive promoters are utilized. Additional regulatory sequences upstream and/or downstream from the core promoter sequence may be included in expression constructs of transformation vectors to bring about varying levels of constitutive expression of heterologous nucleotide sequence in a transgenic plant.

Frequently it is desirable to have constitutive expression of a DNA sequence throughout the cells of an organism. For example, increasing resistance of a plant to infection by soil- and air-borne pathogens might be accomplished by genetic manipulation of the plant's genome to comprise a constitutive promoter operably linked to a heterologous pathogen-resistance gene such that pathogen-resistance proteins are continuously expressed throughout the plant's tissues.

Alternatively, it might be desirable to inhibit expression of a native DNA sequence within a plant's tissues to achieve a desired phenotype. In this case, such inhibition might be accomplished with transformation of the plant to comprise a constitutive promoter operably linked to an antisense nucleotide sequence, such that constitutive expression of the antisense sequence produces an RNA transcript that interferes with translation of the mRNA of the native DNA sequence.

Thus, isolation and characterization of constitutive promoters that can serve as regulatory regions for constitutive expression of heterologous nucleotide sequences of interest are needed for genetic manipulation of plants to exhibit specific phenotypic traits.

In the present invention, a new NPR1 polynucleotide isolated from maize is disclosed. By manipulation of the NPR1 polynucleotide in maize or in other plants, the plant can become resistant to a number of plant pathogens. The present invention provides a new method of conferring disease resistance to plants. In addition, the present invention provides promoter regulatory elements associated with the maize NPR1 polynucleotide that confer constitutive expression on a heterologous polynucleotide and are also capable of inducing expression of the heterologous polynucleotide to a higher level in the presence of a pathogen or fungal elicitor. Further, the present invention describes a method for evaluating putative activators of the plant defense pathway.

SUMMARY OF THE INVENTION

Generally, it is the object of the present invention to provide nucleic acids and proteins relating to NPR1. It is an object of the present invention to provide transgenic plants comprising the nucleic acids of the present invention. It is another object of the present invention to provide methods for modulating, in a transgenic plant, the expression of the nucleic acids of the present invention. Another object of the present invention it to provide promoters capable of driving expression in a constitutive manner, which are also inducible in the presence of a pathogen or fungal elicitor. An additional object of the present invention is to provide methods for screening putative activators of a plant resistance pathway.

Therefore, in one aspect, the present invention relates to an isolated nucleic acid comprising a member selected from the group consisting of (a) a polynucleotide encoding a polypeptide of the present invention; (b) a polynucleotide amplified from a Zea mays nucleic acid library using the primers of the present invention; (c) a polynucleotide comprising at least 20 contiguous bases of the polynucleotides of the present invention; (d) a polynucleotide encoding a maize NPR1 protein; (e) a polynucleotide having at least 70% sequence identity to the polynucleotides of the present invention; (f) a polynucleotide comprising at least 25 nucleotides in length which hybridizes under low stringency conditions to the polynucleotides of the present invention; (g) a polynucleotide comprising the sequence set forth in SEQ ID NOS: 1 or 3; and (f) a polynucleotide complementary to a polynucleotide of (a) through (g). The isolated nucleic acid can be DNA. The isolated nucleic acid can also be RNA.

In another aspect, the present invention relates to vectors comprising the polynucleotides of the present invention. Also, the present invention relates to recombinant expression cassettes, comprising a nucleic acid of the present invention operably linked to a promoter.

In another aspect, the present invention is directed to a host cell into which has been introduced the recombinant expression cassette.

In yet another aspect, the present invention relates to a transgenic plant or plant cell comprising a recombinant expression cassette with a promoter operably linked to any of the isolated nucleic acids of the present invention. Preferred plants containing the recombinant expression cassette of the present invention include but are not limited to maize, soybean, sunflower, sorghum, canola, wheat, alfalfa, cotton, rice, barley, and millet. The present invention also provides transgenic seed from the transgenic plant.

In another aspect, the present invention relates to an isolated protein selected from the group consisting of (a) a polypeptide comprising at least 25 contiguous amino acids of SEQ ID NO: 2 or 4; (b) a polypeptide which is a maize NPR1; (c) a polypeptide comprising at least 70% sequence identity to SEQ ID NO: 2 or 4; (d) a polypeptide encoded by a nucleic acid of the present invention; and (e) a polypeptide characterized by SEQ ID NO: 2 or 4.

In a further aspect, the present invention relates to a method of modulating the level of protein in a plant by introducing into a plant cell a recombinant expression cassette comprising a polynucleotide of the present invention operably linked to a promoter; culturing the plant cell under plant growing conditions to produce a regenerated plant; and inducing expression of the polynucleotide for a time sufficient to modulate the protein of the present invention in the plant. Preferred plants of the present invention include but are not limited to maize, soybean, sunflower, sorghum, canola, wheat, alfalfa, cotton, rice, barley, and millet. The level of protein in the plant can either be increased or decreased.

The present invention also provides for an isolated nucleic acid molecule selected from the group consisting of: a) a nucleic acid driving expression of a gene for a maize NPR1; b) a nucleic acid comprising at least 20 contiguous nucleotides of the sequence set forth in SEQ ID NO: 5; c) a nucleic acid having at least 70% sequence identity to the nucleotide sequence set forth in SEQ ID NO: 5; d) a nucleic acid set forth in SEQ ID NO: 5; and e) a nucleic acid that hybridizes to any of a), b), c), or d) under stringent conditions. The present invention also includes recombinant expression cassettes, vectors, host cells including plant cells, plants and seeds containing the previously described nucleic acid molecule capable of initiating constitutive transcription in a plant cell.

Additionally, the present invention provides for a method for constitutively expressing a heterologous nucleic acid in a plant, comprising introducing into a plant cell or tissue a promoter of the present invention; and culturing the transgenic plant cell or tissue under plant growing conditions to produce a regenerated plant.

In another aspect, the present invention provides for a method of conferring disease resistance to a plant, the method comprising introducing into a plant cell or tissue a vector comprising a maize NPR1 polynucleotide operably linked to a promoter; culturing the transgenic plant cell or tissue under plant growing conditions to produce a regenerated plant; and inducing expression of the maize NPR1 polynucleotide for a time sufficient to confer disease resistance to a plant.

The present invention also provides for a method for screening putative activators of a plant resistance pathway comprising selecting an putative activator gene to test; introducing a plant cell or tissue with an expression cassette containing the putative activator gene operably linked to a constitutive promoter and an expression cassette containing a scorable marker gene operably linked to an inducible promoter; and scoring the plant cell or tissue to determine if expression of the scorable marker gene has increased. The scorable marker gene is preferably selected from beta-glucuronidase, luciferase, anthocyanin pathway transcriptional activators, and green florescent protein. The inducible promoter may be a wound inducible promoter, a stress inducible promoter, or preferably a pathogen inducible promoter. The method of introducing the expression cassette is optionally by ballistic particle acceleration or by Agrobacterium-mediated delivery.

DETAILED DESCRIPTION OF THE INVENTION

Overview

Figure 1:
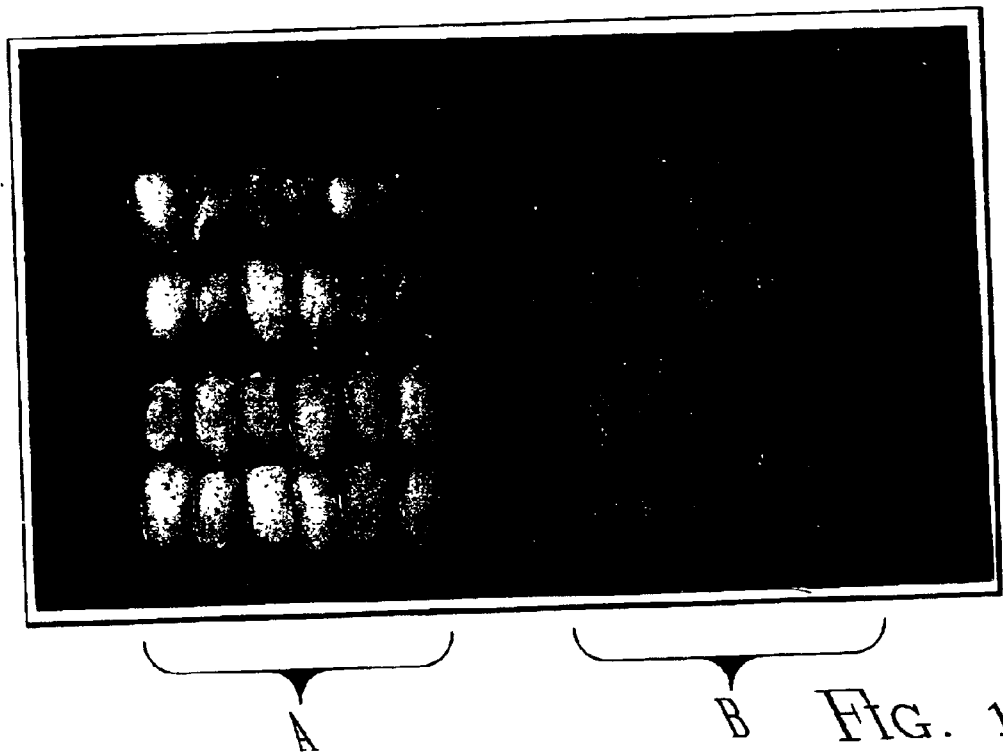
FIG. 1 depicts the results of bombarding maize GS3 embryos with PR1#81::GUS (A) and bombarding maize GS3 embryos with PR1#81::GUS and Ubi::NPR1 (B). The embryos were transferred and cultured in liquid osmotic medium as a control. The embryos were cultured for twenty to twenty-four hours and then subjected to histochemical GUS staining.

The present invention provides, among other things, compositions and methods for modulating (i.e., increasing or decreasing) the level of polynucleotides and polypeptides of the present invention in plants. In particular, the polynucleotides (SEQ ID NOS: 1 and 3) and polypeptides (SEQ ID NOS: 2 and 4) of the present invention can be expressed temporally or spatially, e.g., at developmental stages, in tissues, and/or in quantities, which are uncharacteristic of non-recombinantly engineered plants. Thus, the present invention provides utility in such exemplary applications as disease resistance.

The present invention also provides promoter elements capable of initiating constitutive gene expression. Additionally, the NPR1 promoter is inducible to a higher level of expression in the presence of a pathogen or fungal elicitor. Any polynucleotide of interest, including the polynucleotides of the present invention can be operably linked to the promoter elements of the present invention. The constitutive promoter of the present invention is shown in SEQ ID NO: 5. Methods for isolation of promoter regions are well known in the art. The specific method used to obtain the promoter of the present invention is described in Example 3 below.

In addition, the present invention provides methods for evaluating putative activators of the defense pathway in a plant. The method entails introducing into plant cells or tissues a putative activator gene operably linked to a constitutive promoter and a scorable marker gene operably linked to an inducible promoter.

The present invention also provides isolated nucleic acids comprising polynucleotides of sufficient length and complementarity to a gene of the present invention to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms), orthologs, or paralogs of the gene, or for site directed mutagenesis in eukaryotic cells (see, e.g., U.S. Pat. No. 5,565,350). The isolated nucleic acids of the present invention can also be used for recombinant expression of their encoded polypeptides, or for use as immunogens in the preparation and/or screening of antibodies. The isolated nucleic acids of the present invention can also be employed for use in sense or antisense suppression of one or more genes of the present invention in a host cell, tissue, or plant. Attachment of chemical agents, which bind, intercalate, cleave and/or crosslink to the isolated nucleic acids of the present invention can also be used to modulate transcription or translation. The present invention also provides isolated proteins comprising a polypeptide of the present invention (e.g., preproenzyme, proenzyme, or enzymes).

In addition mutations in the polynucleotides of the present invention will give rise to plants that are sensitive to a wide variety of pathogens and unable to respond to pathogens and chemical inducers of various disease resistance pathways in a plant. These NPRI mutants are useful as "universal disease susceptible" (UDS) plants by virtue of their being susceptible to many strains and pathogens of the host plant and also to pathogens which do not normally infect the host plant, but which infect other hosts. Mutations or suppression of NPR1 can be generated by a variety of methods well known in the art such as, chemical and irradiation mutagenesis, T-DNA insertion, transposon-induced mutagenesis and anti-sense (for a description of generating mutations of NPR1 in Arabidopsis please see PCT application WO9826082, published Jun. 18, 1998 and herein incorporated by reference).

Plants containing NPR1 mutated genes provide useful indicators of the evaluation of disease pressure in field pathogenesis tests where the natural resistance phenotype of so-called wild type (i.e. non-mutant) plants may vary and therefore do not provide a reliable standard of susceptibility. Furthermore, plants containing mutations in NPR1 have the additional utility of testing candidate disease resistance transgenes. Using a NPR1 mutated stock line as a recipient for transgenes; the contribution of the transgene to a disease resistance is directly assessable over a base level of susceptibility. Furthermore, the NPR1 mutated plants are useful as a tool in the understanding of plant-pathogen interactions. NPR1 mutated plants do not mount a systemic response to pathogen attack, and the unabated development of the pathogen is an ideal system in which to study its biological interaction with the host.

Plants with a mutated NPR1 gene may also be susceptible to pathogens outside of the host-range they normally fall. These plants have significant utility in the molecular, genetic, and biological study of host-pathogen interactions. Furthermore, the UDS phenotype also provides plants for fungicide screening. The advantage lies in the UDS phenotype of the mutant, which circumvents the problems encountered by hosts being differentially susceptible to different pathogens and pathotypes, or even resistant to some pathogens or pathotypes. In addition, the NPR1 mutated plants can be used for screening fungicides against a range of pathogens and pathotypes using a heterologous host, i.e. a host that may not normally be within the host species range of a particular pathogen. Thus, the susceptibility of NPR1 mutated plants facilitates efficacious fungicide screening procedures for compounds against important pathogens of crop plants.

The isolated nucleic acids and polypeptides of the present invention can be used over a broad range of plant types, such as, but not limited to, soybean, sunflower, canola, alfalfa, cotton, rice, barley, millet, and particularly monocots such as the species of the family Gramineae including Oryza, Hordeum, Secale, Triticum, Sorghum (e.g., S. bicolor) and Zea (e.g., *Z. mays*). The isolated nucleic acid and proteins of the present invention can also be used in species from the genera: Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Seneclo, Salpiglossis, Cucumis, Browaalia, Glycine, Pisum, Phaseolus, Lolium, Avena, Hordeum, Secale, and Allium.

Pathogens of the invention include, but are not limited to, viruses or viroids, bacteria, insects, fungi, and the like. Viruses include tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Scierotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis*, Fusar-atrum, *Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondite* f.sp. *tritici, Puccinia striiformis, Pyrenophora triticirepentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus; Sunflower: *Plasmophora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* p.v. *Carotovora, Cephalosporium acremonium, Phytophthora cryptogea, Albugo tragopogonis*; Maize: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatie-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganese* subsp. *nebraskense, Trichoderma viride*, Maize Dwarf Mosaic Virus A & B, Wheat Streak Mosaic Virus, Maize Chlorotic Dwarf Virus, *Claviceps sorghi, Pseudonomas avenae, Erwinia chrysanthemi* p.v. *Zea, Erwinia corotovora*, Cornstunt spiroplasma, *Diplodia macrospora, Sclerophthora macrospora, Peronoscierospora sorghi, Peronosclerospora philippinesis, Peronosclerospora maydis, Peronosclerospora sacchari, Spacelotheca reiliana, Physopella zeae, Cephalosporium maydis, Caphalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternate, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.

Plasmids containing the polynucleotide sequences of the invention were deposited on Apr. 16, 1999 with the American Type Culture Collection (ATCC), Manassas, Va., and assigned Accession No. 207204 and 207205. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. § 112.

BRIEF DESCRIPTION OF THE SEQUENCES IN THE SEQUENCE LISTING

SEQ ID NO: 1 Maize NPR1 cDNA sequence

SEQ ID NO: 2 Translated protein sequence of the maize NPR1 cDNA sequence

SEQ ID NO: 3 Maize NPR1 genomic sequence including promoter region

SEQ ID NO: 4 Translated protein sequence of the maize NPR1 genomic sequence

SEQ ID NO: 5 Maize NPR1 promoter region

SEQ ID NO: 6 Oligo nucleotide used in cDNA library construction

DEFINITIONS

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-lefter symbols recommended by the IUPAC-IUB Biochemical Nomenclature Commission. Nucleotides, likewise, may be referred to by their commonly accepted single-letter codes. The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

As used herein, "antisense orientation" includes reference to a duplex polynucleotide sequence, which is operably linked to a promoter in an orientation where the antisense strand is transcribed. The antisense strand is sufficiently complementary to an endogenous transcription product such that translation of the endogenous transcription product is often inhibited.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17: 477–498 (1989)). Thus, the maize preferred codon for a particular amino acid might be derived from known gene sequences from maize. Maize codon usage for 28 genes from maize plants are listed in Table 4 of Murray et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell, which contains a vector and supports the replication and/or expression of the vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is: substantially or essentially free from components that normally accompany or interact with it as found in its naturally occurring environment. The isolated material optionally comprises material not found with the material in its natural environment; or if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids, which are "isolated", as defined herein, are also referred to as "heterologous" nucleic acids.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants, which can be used in the methods of the invention, is generally as broad as the class of higher plants amenable to transformation techniques, including both monocotyledonous and dicotyledonous plants. Preferred plants include, but are not limited to maize, soybean, sunflower, sorghum, canola, wheat, alfalfa, cotton, rice, barley, and millet. A particularly preferred plant is maize (*Zea mays*).

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, underexpressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA—DNA hybrids, the $T_m$ can be approximated from the equation of Meinkoth and Wahl, Anal. Biochem., 138:267–284 (1984): $T_m=81.5°$ C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995).

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence, for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48: 443 (1970); by the search for similarity method of Pearson and Lipman, Proc. Natl. Acad. Sci. 85: 2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, *CABIOS* 5:151–153(1989); Corpet, et al., *Nucleic Acids Research* 16:10881–90 (1988); Huang, et al., *Computer Applications in the Biosciences* 8: 155–65 (1992), and Pearson, et al., *Methods in Molecular Biology* 24: 307–331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-lnterscience, New York (1995).

GAP uses the algorithm of Needleman and Wunsch (*J Mol Biol* 48: 443–453 (1970)) to find the alignment of two complete sequences that maximizes the number of matches and minimizes the number of gaps. GAP considers all possible alignments and gap positions and creates the alignment with the largest number of matched bases and the fewest gaps. Default gap creation penalty values and gap extension penalty values in Version 10 of the Wisconsin Genetics Software Package are 8 and 2, respectively, for protein sequences. For nucleotide sequences, the default gap creation penalty is 50 while the default gap extension penalty is 3. The gap creation and gap extension penalties can be expressed as an integer selected form the group of integers consisting of form 0 to 100. Thus, for example, the gap creation and gap extension penalties can be 0, 1, 2, 3, 4, 5, 6, 7, 8, 9, 10, 15, 20, 30, 40, 50, 60, or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff, *Proc Natl Acad Sci USA* 89:10915).

Unless otherwise stated, sequence identity/similarity values provided herein refer to the value obtained using the BLAST 2.0 suite of programs using default parameters. Altschul et al., *Nucleic Acids Res.* 25:3389–3402 (1997) or GAP version 10 of Wisconsin Genetic Software Package using default parameters. Software for performing BLAST analyses is publicly available, e.g., through the National Center for Biotechnology Information (www.ncbi.nlm.nih.gov/). This algorithm involves first identifying high scoring sequence pairs (HSPs) by identifying short words of length W in the query sequence which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89: 10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5877 (1993)). One measure of similarity provided by the BLAST algorithm is the smallest sum probability (P(N)), which provides an indication of the probability that a match between two nucleotides or two amino acid sequences would occur by chance.

BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Clayerie and States, *Comput. Chem.*, 17:191–201 (1993)) low-complexity filters can be employed alone or in combination.

(c) As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity". Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4:11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Nucleic Acids

The present invention provides, among other things, isolated nucleic acids of RNA, DNA, and analogs and/or chimeras thereof, comprising a polynucleotide of the present invention.

A polynucleotide of the present invention is inclusive of:
  (a) a polynucleotide encoding a polypeptide of SEQ ID NOS: 2 or 4 and conservatively modified and polymorphic variants thereof, including exemplary polynucleotides of SEQ ID NOS: 1 and 3;
  (b) a polynucleotide which is the product of amplification from a *Zea mays* nucleic acid library using primer pairs which selectively hybridize under stringent conditions to loci within a polynucleotide selected from SEQ ID NOS: 1 and 3, wherein the polynucleotide has substantial sequence identity to a polynucleotide selected from SEQ ID NOS: 1 and 3;
  (c) a polynucleotide which selectively hybridizes to a polynucleotide of (a) or (b);
  (d) a polynucleotide having a specified sequence identity with polynucleotides of (a), (b), or (c);
  (e) complementary sequences of polynucleotides of (a), (b), (c), or (d); and
  (f) a polynucleotide comprising at least a specific number of contiguous nucleotides from a polynucleotide as shown in SEQ ID NO: 1 or 3.

A. Polynucleotides Encoding a Polypeptide of the Present Invention or Conservatively Modified or Polymorphic Variants Thereof The present invention provides isolated nucleic acids comprising a polynucleotide of the present invention, wherein the polynucleotide encodes a polypeptide of the present invention, or conservatively modified or polymorphic variants thereof. Accordingly, the present invention includes polynucleotides of SEQ ID NOS: 1 and 3, and silent variations of polynucleotides encoding a polypeptide of SEQ ID NOS: 2 and 4. Additionally, the present invention further provides isolated nucleic acids comprising polynucleotides encoding one or more allelic (polymorphic) variants of polypeptides/polynucleotides. Polymorphic variants are frequently used to follow segregation of chromosomal regions in, for example, marker assisted selection methods for crop improvement.

B. Polynucleotides Amplified from a *Zea mays* Nucleic Acid Library

The present invention provides an isolated nucleic acid comprising a polynucleotide of the present invention, wherein the polynucleotides are amplified from a *Zea mays* nucleic acid library. *Zea mays* lines B73, PHRE1, A632, BMS-P2#10, W23, and Mo17 are known and publicly available. Other publicly known and available maize lines can be obtained from the Maize Genetics Cooperation (Urbana, Ill.). The nucleic acid library may be a cDNA library, a genomic library, or a library generally constructed from nuclear transcripts at any stage of intron processing. cDNA libraries can be normalized to increase the representation of relatively rare cDNAs. In optional embodiments, the cDNA library is constructed using a full-length cDNA synthesis method. Examples of such methods include Oligo-Capping (Maruyama, K. and Sugano, S. *Gene* 138:171–174, 1994), Biotinylated CAP Trapper (Carninci, P., Kvan, C., et al. *Genomics* 37: 327–336, 1996), and CAP Retention Procedure (Edery, E., Chu, L. L., et al. *Molecular and Cellular Biology* 15: 3363–3371,1995). cDNA synthesis is often catalyzed at 50–55° C. to prevent formation of RNA secondary structure. Examples of reverse transcriptases that are relatively stable at these temperatures are SuperScript II Reverse Transcriptase (Life Technologies, Inc.), AMV Reverse Transcriptase (Boehringer Mannheim) and Retro-Amp Reverse Transcriptase (Epicentre). Rapidly growing tissues, or rapidly dividing cells are preferably used as mRNA sources. Preferred tissue for use as a mRNA source is young maize shoot tissue.

The present invention also provides subsequences of the polynucleotides of the present invention. A variety of subsequences can be obtained using primers which selectively hybridize under stringent conditions to at least two sites within a polynucleotide of the present invention, or to two sites within the nucleic acid which flank and comprise a polynucleotide of the present invention, or to a site within a polynucleotide of the present invention and a site within the nucleic acid which comprises it. Primers are chosen to selectively hybridize, under stringent hybridization conditions, to a polynucleotide of the present invention. Generally, the primers are complementary to a subsequence of the target nucleic acid, which they amplify. As those skilled in the art will appreciate, the sites to which the primer pairs will selectively hybridize are chosen such that a single contiguous nucleic acid can be formed under the desired amplification conditions.

In optional embodiments, the primers will be constructed so that they selectively hybridize under stringent conditions to a sequence (or its complement) within the target nucleic acid which comprises the codon encoding the carboxy or amino terminal amino acid residue (i.e., the 3' terminal coding region and 5' terminal coding region, respectively) of the polynucleotides of the present invention. Optionally within these embodiments, the primers will be constructed to selectively hybridize entirely within the coding region of the target polynucleotide of the present invention such that the product of amplification of a cDNA target will consist of the coding region of that cDNA. The primer length in nucleotides is selected from the group of integers consisting of from at least 15 to 50. Thus, the primers can be at least 15, 18, 20, 25, 30, 40, or 50 nucleotides in length. Those of skill will recognize that a lengthened primer sequence can be employed to increase specificity of binding (i.e., annealing) to a target sequence. A non-annealing sequence at the 5' end of a primer (a "tail") can be added, for example, to introduce a cloning site at the terminal ends of the amplicon.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity), or verifying the presence of one or more linear epitopes which are specific to a polypeptide of the present invention. Methods for protein synthesis from PCR derived templates are known in the art and available commercially. See, e.g., Amersham Life Sciences, Inc, Catalog '97, p.354.

Methods for obtaining 5' and/or 3' ends of a vector insert are well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego), pp. 28–38 (1990)); see also, U.S. Pat. No. 5,470,722, and *Current Protocols in Molecular Biology*, Unit 15.6, Ausubel, et al., Eds, Greene Publishing and Wiley-lnterscience, New York (1995); Frohman and Martin, *Techniques* 1:165 (1989).

C. Polynucleotides which Selectively Hybridize to a Polynucleotide of (A) or (B)

The present invention provides isolated nucleic acids comprising polynucleotides of the present invention, wherein the polynucleotides selectively hybridize, under selective hybridization conditions, to a polynucleotide of sections (A) or (B) as discussed above. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: corn, canola, soybean, cotton, wheat, sorghum, sunflower, oats, sugar cane, millet, barley, and rice. Optionally, the cDNA library comprises at least 80% full-length sequences, preferably at least 85% or 90% full-length sequences, and more preferably at least 95% full-length sequences. The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

D. Polynucleotides Having a Specific Sequence Identity with the Polynucleotides of (A), (B) or (C)

The present invention provides isolated nucleic acids comprising polynucleotides of the present invention, wherein the polynucleotides have a specified identity at the nucleotide level to a polynucleotide as disclosed above in sections (A), (B), or (C), above. Identity can be calculated using, for example, the BLAST or GAP algorithms under default conditions. The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

E. Polynucleotides Complementary to the Polynucleotides of (A)–(D)

The present invention provides isolated nucleic acids comprising polynucleotides complementary to the polynucleotides of paragraphs A–D, above. As those of skill in the art will recognize, complementary sequences base pair throughout the entirety of their length with the polynucleotides of sections (A)–(D) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

F. Polynucleotides which are Subsequences of the Polynucleotides of (A)–(E)

The present invention provides isolated nucleic acids comprising polynucleotides, which comprise at least 15 contiguous bases from the polynucleotides of as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 85, 90, 95, 100, 110, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, or 1000 contiguous nucleotides in length from the polynucleotides of (A)–(E). Optionally, the number of such subsequences encoded by a polynucleotide of the instant embodiment can be any integer selected from the group consisting of from 1 to 1000, such as 2, 3, 4, or 5. The subsequences can be separated by any integer of nucleotides from 1 to the number of nucleotides in the sequence such as at least 5, 10, 15, 20, 25, 30, 35, 40, 45, 50, 75, 100, 200, 300, 400, 500, 600, 700, 800, 900, or 1000 nucleotides.

Subsequences can be made by in vitro synthetic, in vitro biosynthetic, or in vivo recombinant methods. In optional embodiments, subsequences can be made by nucleic acid amplification. For example, nucleic acid primers will be constructed to selectively hybridize to a sequence (or its complement) within, or co-extensive with, the coding region.

The subsequences of the present invention can comprise structural characteristics of the sequence from which it is derived. Alternatively, the subsequences can lack certain structural characteristics of the larger sequence from which it is derived such as a poly (A) tail. Optionally, a subsequence from a polynucleotide encoding a polypeptide having at least one linear epitope in common with a prototype polypeptide sequence as provided in (a), above, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot. In preferred embodiments, the monocot is *Zea mays*.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known and extensively described in the art. For a description of various nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. While isolation of RNA, and construction of cDNA and genomic libraries is well known to those of ordinary skill in the art, the following highlights some of the methods employed.

A1. mRNA Isolation and Purification

Total RNA from plant cells comprises such nucleic acids as mitochondrial RNA, chloroplastic RNA, rRNA, tRNA, hnRNA and mRNA. Total RNA preparation typically involves lysis of cells and removal of organelles and proteins, followed by precipitation of nucleic acids. Extraction of total RNA from plant cells can be accomplished by a variety of means. Frequently, extraction buffers include a strong detergent such as SDS and an organic denaturant such as guanidinium isothiocyanate, guanidine hydrochloride or phenol. Following total RNA isolation, poly(A)$^+$ mRNA is typically purified from the remainder RNA using oligo(dT) cellulose. Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-lnterscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli Inc., PA). See also, U.S. Pat. Nos. 5,614,391; and, 5,459,253. The mRNA can be fractionated into populations with size ranges of about 0.5, 1.0, 1.5, 2.0, 2.5 or 3.0 kb. The cDNA synthesized for each of these fractions can be size selected to the same size range as its mRNA prior to vector insertion. This method helps eliminate truncated cDNA formed by incompletely reverse transcribed mRNA.

A2. Construction of a cDNA Library

Construction of a cDNA library generally entails five steps. First, first strand cDNA synthesis is initiated from a poly(A)+mRNA template using a poly(dT) primer or random hexanucleotides. Second, the resultant RNA-DNA hybrid is converted into double stranded cDNA, typically by reaction with a combination of RNAse H and DNA polymerase I (or Klenow fragment). Third, the termini of the double stranded cDNA are ligated to adaptors. Ligation of the adaptors can produce cohesive ends for cloning. Fourth, size selection of the double stranded cDNA eliminates excess adaptors and primer fragments, and eliminates partial cDNA molecules due to degradation of mRNAs or the failure of reverse transcriptase to synthesize complete first strands. Fifth, the cDNAs are ligated into cloning vectors and packaged. cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-lnterscience, New York (1995). cDNA synthesis kits are available from a variety of commercial vendors such as Stratagene or Pharmacia.

A number of cDNA synthesis protocols have been described which provide substantially pure full-length cDNA libraries. Substantially pure full-length cDNA libraries are constructed to comprise at least 90%, and more preferably at least 93% or 95% full-length inserts amongst clones containing inserts. The length of insert in such libraries can be from 0 to 8, 9, 10, 11, 12, 13, or more kilobase pairs. Vectors to accommodate inserts of these sizes are known in the art and available commercially. See, e.g., Stratagene's lambda ZAP Express (cDNA cloning vector with 0 to 12 kb cloning capacity).

An exemplary method of constructing a greater than 95% pure full-length cDNA library is described by Carninci et al., *Genomics*, 37:327–336 (1996). In that protocol, the cap-structure of eukaryotic mRNA is chemically labeled with biotin. By using streptavidin-coated magnetic beads, only the full-length first-strand cDNA/mRNA hybrids are selectively recovered after RNase I treatment. The method provides a high yield library with an unbiased representation of the starting mRNA population. Other methods for producing full-length libraries are known in the art. See, e.g., Edery et al., *Mol. Cell Biol.*, 15(6):3363–3371 (1995); and, PCT Application WO 96/34981.

A3. Normalized or Subtracted cDNA Libraries

A non-normalized cDNA library represents the mRNA population of the tissue it was made from. Since unique clones are out-numbered by clones derived from highly expressed genes, their isolation can be laborious. Normalization of a cDNA library is the process of creating a library in which each clone is more equally represented.

A number of approaches to normalize cDNA libraries are known in the art. One approach is based on hybridization to genomic DNA. The frequency of each hybridized cDNA in the resulting normalized library would be proportional to that of each corresponding gene in the genomic DNA. Another approach is based on kinetics. If cDNA reannealing follows second-order kinetics, rarer species anneal less rapidly and the remaining single-stranded fraction of cDNA becomes progressively more normalized during the course of the hybridization. Specific loss of any species of cDNA, regardless of its abundance, does not occur at any Cot value. Construction of normalized libraries is described in Ko,

*Nucl. Acids. Res.,* 18(19):5705–5711 (1990); Patanjali et al., *Proc. Natl. Acad. U.S.A.,* 88:1943–1947 (1991); U.S. Pat. Nos. 5,482,685, and 5,637,685. In an exemplary method described by Soares et a., normalization resulted in reduction of the abundance of clones from a range of four orders of magnitude to a narrow range of only 1 order of magnitude. *Proc. Natl. Acad. Sci. USA,* 91:9228–9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote et al. in, *Plant Molecular Biology: A Laboratory Manual*, Clark, Ed., Springer-Verlag, Berlin (1997); Kho and Zarbl, *Technique*, 3(2):58–63 (1991); Sive and St. John, *Nucl. Acids Res.,* 16(22):10937 (1988); *Current Protocols in Molecular Biology*, Ausubel, et al., Eds., Greene Publishing and Wiley-Interscience, New York (1995); and, Swaroop et al., *Nucl. Acids Res.,* 19)8):1954 (1991). cDNA subtraction kits are commercially available. See, e.g., PCR-Select (Clontech, Palo Alto, Calif.).

A4. Construction of a Genomic Library

To construct genomic libraries, large segments of genomic DNA are generated by fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

A5. Nucleic Acid Screening and Isolation Methods

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques,* 22(3): 481–486 (1997). In that method, a primer pair is synthesized with one primer annealing to the 5' end of the sense strand of the desired cDNA and the other primer to the vector. Clones are pooled to allow large-scale screening. By this procedure, the longest possible clone is identified amongst candidate clones. Further, the PCR product is used solely as a diagnostic for the presence of the desired cDNA and does not utilize the PCR product itself. Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang et al., *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.* 22: 1859–1862 (1981); the solid phase phosphoramidite triester method described by Beaucage and Caruthers, *Tetra. Letts.* 22(20): 1859–1862 (1981), e.g., using an automated synthesizer, e.g., as described in Needham-VanDevanter et al., *Nucleic Acids Res.,* 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is best employed for sequences of about 100 bases or less, longer sequences may be obtained by the ligation of shorter sequences.

The NPR1 Promoter

The promoters for NPR1 genes may be generally isolated from the 5' untranslated region flanking their respective transcription initiation sites. Methods for isolation of promoter regions are well known in the art. By "isolated" is intended that the promoter sequences have been determined and can be extracted by molecular techniques or synthesized by chemical means. In either instance, the promoter is removed from at least one of its flanking sequences in its native state. The sequence for the promoter region of the maize NPR1 can be found in SEQ ID NO: 5.

It is recognized that regions in addition to the promoter region may be used to initiate transcription. Such regions include the UTR and even portions of the coding sequence particularly 5' portions of the coding region. Generally, from about 3 nucleotides (1 codon) up to about 150 nucleotides (50 codons) of the 5' coding region can be used. See, for example, McElroy et al. (1991) *Mol. Gen. Genet.* 231: 150–160 and herein incorporated by reference, where expression vectors were constructed based on the rice actin 15' region.

Comparable promoter regions from other plants may be obtained by utilization of the coding or promoter sequences of the invention. Using the NPR1 coding sequences, other NPR1 promoters can be isolated by obtaining regions 5' to the regions of homology.

Methods are readily available in the art for the hybridization of nucleic acid sequences. Promoter sequences from other plants may be isolated according to well known techniques based on their sequence homology to the promoter sequences set forth herein. In these techniques, all or part of the known promoter sequence is used as a probe, which selectively hybridizes to other sequences present in a population of cloned genomic DNA, fragments (i.e. genomic libraries) from a chosen organism.

For example, the entire promoter sequence or portions thereof may be used as probes capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes may be used to amplify corresponding promoter sequences from a chosen organism by the well-known process of polymerase chain reaction (PCR). This technique may be used to isolate additional promoter sequences from a desired organism or as a diagnostic assay to determine the presence of the promoter sequence in an organism.

Such techniques include hybridization screening of plated DNA libraries (either plaques or colonies; see e.g. Innis et al. (1990) *PCR Protocols. A Guide to Methods and Applications*, eds., Academic Press).

The isolated promoter sequences of the present invention can be modified to provide for a range of expression levels of the heterologous nucleotide sequence. Thus, less than the entire promoter regions may be utilized and the ability to drive developmentally regulated expression retained. However, it is recognized that expression levels of mRNA may be altered and usually decreased with deletions of portions of the promoter sequences. Generally, at least about 20 nucleotides of an isolated promoter sequence will be used to drive expression of a nucleotide sequence. "Variants" of the disclosed sequences, such as those that result from site-directed mutagenesis, as well as synthetically derived sequences are also considered part of the present invention. Methods for mutagenesis and nucleotide sequence alterations are well known in the art. See, for example, Kunkel (1985) *Proc Natl Acad Sci USA* 82:488–492 (1985); Kunkel et al., *Methods Enzymol* 154:367–382 (1987); U.S. Pat. No. 4,873,192; Walker et al., eds. (1983) *Techniques in Molecular Biology* (MacMillan Publishing Company, New York) and the references cited therein. Thus, the promoter nucleotide sequences of the invention include both the naturally occurring sequences as well as mutant and synthetically derived forms. Generally, nucleotide sequence variants of the invention will have at least about 50%, 60%, to 70%, generally about 80%, preferably about 85%, 90%, up to 98% sequence identity to its respective native nucleotide sequence.

Fragments of the promoter nucleotide sequences disclosed herein are also encompassed by the present invention. By "fragment" is intended a portion of the promoter nucleotide sequence. Fragments of a promoter nucleotide sequence may retain their biological activity. Thus, for example, less than the entire promoter sequences disclosed herein may be utilized to drive expression of an operably linked nucleotide sequence of interest, such as a nucleotide sequence encoding a heterologous protein. It is within the skill of one in the art to determine whether such fragments decrease expression levels or alter the nature of expression, i.e. constitutive expression. Alternatively, fragments of a promoter nucleotide sequence that are useful as hybridization probes generally do not retain this biological activity.

Nucleic acid molecules that are fragments of a promoter nucleotide sequence comprise at least 15, 20, 25, 30, 35, 40, 45, 50, 75, 100, 325, 350, 375, 400, 425, 450, 500, 550, 600, 650, 700, 800, 900, 1,000, 1,100, 1,200, 1,300, 1,400, 1,500, 1,600, or 1,700 nucleotides, or up to the number of nucleotides present in a full-length promoter nucleotide sequence disclosed herein. Generally, fragments of a promoter sequence that retain their biological activity comprise at least 30, 35, or 40 contiguous nucleotides, still more preferably at least 100 contiguous nucleotides of the particular promoter nucleotide sequence disclosed herein. Preferred fragment lengths depend upon the objective and will vary depending upon the particular promoter sequence.

The nucleotides of such fragments will usually comprise the TATA recognition sequence of the particular promoter sequence. Such fragments may be obtained by use of restriction enzymes to cleave the naturally occurring promoter nucleotide sequence disclosed herein; by synthesizing a nucleotide sequence from the naturally occurring sequence of the promoter DNA sequence; or may be obtained through the use of PCR technology. Variants of these promoter fragments, such as those resulting from site-directed mutagenesis, are encompassed by the compositions of the present invention.

It is recognized that to increase transcription levels enhancers may be utilized in combination with the promoter regions of the invention. Enhancers are nucleotide sequences that act to increase the expression of a promoter region. Enhancers are known in the art.

Modifications of the isolated promoter sequences of the present invention can provide for a range of expression of the heterologous nucleotide sequence. Thus, they may be modified to be weak promoters or strong promoters. Generally, by "weak promoter" is intended a promoter that drives expression of a coding sequence at a low level. By "low level" is intended at levels of about $1/10,000$ transcripts to about $1/100,000$ transcripts to about $1/500,000$ transcripts. Conversely, a strong promoter drives expression of a coding sequence at a high level, or at about $1/10$ transcripts to about $1/100$ transcripts to about $1/1000$ transcripts.

Nucleotide sequences comprising at least about 20 contiguous nucleotides of the sequence set forth in SEQ ID NO: 5 are encompassed. These sequences may be isolated by hybridization, PCR, and the like. Such sequences encompass fragments capable of driving constitutive expression, fragments useful as probes to identify similar sequences, as well as elements responsible for expression. Biologically active variants of the promoter sequences are also encompassed by the method of the present invention. Such variants should retain promoter activity, particularly the ability to drive constitutive expression. Biologically active variants include, for example, the native promoter sequences of the invention having one or more nucleotide substitutions, deletions or insertions. Promoter activity may be measured by Northern blot analysis, reporter activity measurements when using transcriptional fusions, and the like. See, for example, Sambrook et al. (1989) *Molecular Cloning: A Laboratory Manual* ($2^{nd}$ ed. Cold Spring Harbor Laboratory, Cold Spring Harbor, N.Y.), herein incorporated by reference.

The coding sequence expressed by the promoters of the invention may be used to express proteins in a constitutive manner and to increase constitutive expression in response to a pathogen. The affect of various expressed proteins of interest include but are not limited to alterations in development, male or female fertility, resistance to insects, resistance to disease, agronomic traits and the like.

These results can be achieved by providing expression of heterologous or increased expression of endogenous products in the plant. Alternatively, the results can be achieved by providing for a reduction of expression of one or more endogenous products, particularly enzymes and cofactors in the plant. These changes result in a change in the phenotype of the transformed plant. For example, the promoter sequences of the invention can be used to express insect toxic proteins. Alternatively, the promoter sequences of the invention can be used to produce antisense mRNA complementary to the coding sequence of an essential protein, and inhibit production of the protein.

General categories of genes of interest for the purposes of the present invention include for example, those genes involved in information, such as Zinc fingers, those involved in communication, such as kinases, and those involved in housekeeping, such as heat shock proteins. It is recognized that the genes of interest depend on the exact specificity of the NPR1 promoter.

More specific categories of transgenes are, for example, genes involved in resistance to disease, pesticides, herbicides and insect pests; sterility genes, quality of grain traits, or commercial traits. It is recognized that any gene of interest can be operably linked to the promoter of the inventions and expressed in a constitutive manner.

Genes involved in resistance to insects may encode resistance to insect pests such as second generation corn borer (*Ostinia nubilalis*) and adult rootworm beetle (*Diabrotica virgifera*). Such genes include, for example, *Bacillus thuringiensis* endotoxin genes (U.S. Pat. Nos. 5,366,892; 5,747,450; 5,737,514; 5,723,756; 5,593,881; Geiser et al., *Gene* 48:109 (1986); lectins (Van Damme et al., *Cell* 78:1089 (1994); and the like.

Gene encoding resistance to disease traits may include detoxification genes such as fumonisin esterase (U.S. Pat. Nos. 5,792,931 and 5,716,820); avirulence (avr) and disease resistance (R) genes (Jones et al., *Science* 266:789 (1994); Martin et al., *Science* 262:1432 (1993); Mindrinos et al., *Cell* 78:1089 (1994)); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g. the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins, described in U.S. Pat. No. 5,703,409 provide a description of modifications of proteins for desired purposes.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase) and acetoacetyl-CoA reductase (see Schubert et al., *J Bacteriol* 170:5837–5847 (1988)) facilitate expression of polyhyroxy-alkanoates (PHAs).

Exogenous products include plant enzymes and products as well as those from other sources including prokaryotes and other eukaryotes. Such products include enzymes, cofactors, hormones, and the like.

The heterologous nucleotide sequence operably linked to one of the promoters disclosed herein may be an antisense sequence for a targeted gene. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is invited to achieve a desired phenotypic response. Thus, the promoter sequences disclosed herein may be operably linked to antisense DNA sequence to reduce or inhibit expression of a native protein in the plant.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A number of promoters can be used in the practice of the invention. A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 (Ubi) promoter (Christensen, et al. *Plant Mol Biol* 18, 675–689 (1992); Bruce, et al., *Proc Natl Acad Sci USA* 86, 9692–9696 (1989)), the Smas promoter, the cinnamyl alcohol dehydrogenase promoter (U.S. Pat. No. 5,683,439), the Nos promoter, the pEmu promoter, the rubisco promoter, the GRP1-8 promoter, the maize constitutive promoters described in PCT Publication No. WO 99/43797 which include the histone H2B, metallothionein, alpha-tubulin 3, elongation factor efla, ribosomal protein rps8, chlorophyll a/b binding protein, and glyceraldehyde-3-phosphate dehydrogenase promoters, and other transcription initiation regions from various plant genes known to those of skill. For constitutive expression of the polynucleotides of the present invention, the ubiquitin I promoter is the preferred promoter.

Where low level expression is desired, weak promoters will be used. It is recognized that weak inducible promoters may be used. Additionally, either a weak constitutive or a weak tissue specific promoter may be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompass promoters that are expressed in only a few cells and not in others to give a total low level of expression. Such weak constitutive promoters include, for example, the core promoter of the Rsyn7 (PCT Publication No. WO 97/44756), the core 35S CaMV promoter, and the like. Where a promoter is expressed at unacceptably high levels, portions of the promoter sequence can be deleted or modified to decrease expression levels.

Alternatively, the plant promoter can direct expression of a polynucleotide of the present invention under environmental control. Such promoters are referred to here as "inducible" promoters. Environmental conditions that may effect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light. Examples of pathogen-inducible promoters include those from proteins, which are induced following infection by a pathogen; e.g., PR proteins, SAR proteins, beta-1,3-glucanase, chitinase, etc. See, for example, Redolfi, et al., *Neth J. Plant Pathol.* 89:245–254 (1983); Uknes, et al., *The Plant Cell* 4:645–656 (1992); Van Loon, *Plant Mol. Virol.* 4:111–116 (1985); and PCT Publication No. WO 99/43819.

Of interest are promoters that are expressed locally at or near the site of pathogen infection. See, for example, Marineau, et al., *Plant Mol Biol* 9:335–342 (1987); Matton, et al., *Molecular Plant-Microbe Interactions* 2:325–342 (1987); Somsisch et al., *Proc Natl Acad Sci USA* 83:2427–2430 (1986); Somssich et al., *Mole Gen Genetics* 2:93–98 (1988); Yang, *Proc Natl Acad Sci USA* 93:14972–14977. See also, Chen, et al., *Plant J* 10:955–966 (1996); Zhang and Sing, *Proc Natl Acad Sci USA* 91:2507–2511 (1994); Warner, et al., *Plant J* 3:191–201 (1993); and Siebertz, et al., *Plant Cell* 1:961–968 (1989), all of which are herein incorporated by reference. Of particular interest is the inducible promoter for the maize PRms gene, whose expression is induced by the pathogen *Fusarium moniliforme* (see, for example, Cordero, et al., *Physiol Molec Plant Path* 41:189–200 (1992) and is herein incorporated by reference.

Additionally, as pathogens find entry into plants through wounds or insect damage, a wound inducible promoter may be used in the constructs of the invention. Such wound inducible promoters include potato proteinase inhibitor (pin II) gene (Ryan, *Annu Rev Phytopath* 28:425449 (1990); Duan, et a., *Nat Biotech* 14:494–498 (1996)); wun1 and wun2, U.S. Pat. No. 5,428,148; win1 and win2 (Stanford, et al., *Mol Gen Genet* 215:200–208 (1989)); systemin (McGurl, et al., *Science* 225:1570–1573 (1992)); WIP1 (Rohmeier, et al., *Plant Mol Biol* 22:783–792 (1993); Eckelkamp, et al., *FEB Letters* 323:73–76 (1993)); MPI gene (Corderok, et al., *The Plant J* 6(2):141–150(1994)); and the like, herein incorporated by reference.

Examples of promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051), glob-1 promoter, and gamma-zein promoter. The operation of a promoter may also vary depending on its location in the genome. Thus, an inducible promoter may become fully or partially constitutive in certain locations. An inducible promoter can also be modified, if necessary, for weak expression.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in *Zea mays*, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a gene of the present invention so as to control the expression of the gene. Gene expression can be modulated under conditions suitable for plant growth to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8: 4395–4405 (1988); Callis et al., *Genes Dev.* 1: 1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, N.Y. (1994).

The vector comprising the sequences from a polynucleotide of the present invention will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., Meth. in Enzymol., 153:253–277 (1987). These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., Gene, 61:1–11 (1987) and Berger et al., Proc. Natl. Acad. Sci. U.S.A., 86:8402–8406 (1989). Another useful vector herein is plasmid pBI101.2 that is available from Clontech Laboratories, Inc. (Palo Alto, Calif.).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to inhibit gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy et al., *Proc. Nat'l. Acad. Sci.* (*USA*) 85: 8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2: 279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B., et al., *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home, et al., *J Am Chem Soc* (1990) 112:2435–2437. Use of N4, N4-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681941.

Proteins

The isolated proteins of the present invention comprise a polypeptide having at least 10 amino acids encoded by any one of the polynucleotides of the present invention as discussed more fully, above, or polypeptides which are conservatively modified variants thereof. The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

As those of skill will appreciate, the present invention includes catalytically active polypeptides of the present invention (i.e., enzymes). Catalytically active polypeptides have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention, which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

A. Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva, et al., *Gene* 22: 229–235 (1983); Mosbach, et al., *Nature* 302: 543–545 (1983)).

B. Expression in Eukaryotes

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., *Methods in Yeast Genetics*, Cold Spring Harbor Laboratory (1982) is a well recognized work describing the various methods available to produce the protein in yeast. Two widely utilized yeast for production of eukaryotic proteins are *Saccharomyces cerevisiae* and *Pichia pastoris*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative cell cultures useful for the production of peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol. Rev.* 89: 49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See, Schneider, *J. Embryol. Exp. Morphol.* 27: 353–365 (1987).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., *J. Virol.* 45: 773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in *DNA Cloning Vol. II a Practical Approach*, D. M. Glover, Ed., IRL Press, Arlington, Va. pp. 213–238 (1985).

Transfection/Transformation of Cells

The method of transformation/transfection is not critical to the instant invention; various methods of transformation or transfection are currently available. As newer methods are available to transform crops or other host cells they may be directly applied. Accordingly, a variety of methods have been developed to insert a DNA sequence into the genome of a host cell to obtain the transcription and/or translation of the sequence to effect phenotypic changes in the organism. Thus, any method, which provides for effective transformation/transfection may be employed.

The genes of the present invention can be used to transform any plant. In this manner, genetically modified plants, plant cells, plant tissue, seed, and the like can be obtained. Transformation protocols may vary depending on the type of plant cell, i.e. monocot or dicot, targeted for transformation. Suitable methods of transforming plant cells include microinjection (Crossway et al. (1986) *BioTechniques* 4:320–334), electroporation (Riggs et al (1986) *Proc. Natl. Acad. Sci. USA* 83:5602–5606, Agrobacterium mediated transformation (Hinchee et al. (1988) *Biotechnology* 6:915–921), direct gene transfer (Paszkowski et al (1984) *EMBO J.* 3:2717–2722), and ballistic particle acceleration (see, for example, Sanford et al. U.S. Pat. No. 4,945,050; Tomes et al. "Direct DNA Transfer into Intact Plant Cells via Microprojectile Bombardment" In Gamborg and Phillips (Eds.) *Plant Cell, Tissue and Organ Culture: Fundamental Methods*, Springer-Verlag, Berlin (1995); and McCabe et al. (1988) *Biotechnology* 6:923–926). Also see, Weissinger et al. (1988) *Annual Rev. Genet.* 22:421–477; Sanford et al. (1987) *Particulate Science and Technology* 5:27–37 (onion); Christou et al. (1988) *Plant Phisiol.* 87:671–674 (soybean); McCabe et al. (1988) *Bio/Technology* 6:923–926 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes et al. "Direct DNA Transfer into Intact Plant Cells via Microprojectile Bombardment" In Gamborg and Phillips (Eds.) *Plant Cell, Tissue and Organ Culture: Fundamental Methods*, Springer-Verlag, Berlin (1995) (maize); Klein et al. (1988) *Plant Physiol.* 91:440–444 (maize) Fromm et al. (1990) *Biotechnology* 8:833–839 (maize); Hooydaas-Van Slogteren & Hooykaas (1984) *Nature (London)* 311:763–764; Bytebier et al. (1987) *Proc. Natl. Acad. Sci. USA* 84:5345–5349 (Liliaceae); De Wet et al. (1985) In *The Experimental Manipulation of Ovule Tissues* ed. G. P. Chapman et al. pp. 197–209. Longman, N.Y. (pollen); Kaeppler et al. (1990) *Plant Cell Reports* 9:415–418; and Kaeppler et al. (1992) *Theor. Appl. Genet.* 84:560–566 (whisker-mediated transformation); D'Halluin et al. (1992) *Plant Cell* 4:1495–1505 (electroporation); LI et al. (1993) *Plant Cell Reports* 12:250–255 and Christou and Ford (1995) *Annals of Botany* 75:745–750 (maize via *Agrobacterium tumefaciens*); all of which are herein incorporated by reference.

The cells, which have been transformed, may be grown into plants in accordance with conventional ways. See, for example, McCormick et al. (1986) *Plant Cell Reports*, 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, if these parts comprise cells comprising the isolated nucleic acid of the present invention. Progeny, variants, and mutants of the regenerated plants are also included within the scope of the invention, if these parts comprise the introduced nucleic acid sequences.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Backcrossing to a parental plant and out-crossing with a non- transgenic plant are also contemplated.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology. Vol. 2: Special Methods in Peptide Synthesis, Part A*.; Merrifield, et al., *J. Am. Chem. Soc.* 85: 2149–2156 (1963), and Stewart et al, *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide)) is known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: N.Y. (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and includes, for example, radioimmunoassays, Western blotting techniques or immunoprecipitation.

Modulating Polypeptide Levels and/or Composition

The present invention further provides a method for modulating (i.e., increasing or decreasing) the concentration or composition of the polypeptides of the present invention in a plant or part thereof. Modulation can be effected by increasing or decreasing the concentration and/or the composition (i.e., the ratio of the polypeptides of the present invention) in a plant. The method comprises introducing into a plant cell with a recombinant expression cassette comprising a polynucleotide of the present invention as described above to obtain a transformed plant cell, culturing the transformed plant cell under plant cell growing conditions, and inducing or repressing expression of a polynucleotide of the present invention in the plant for a time sufficient to modulate concentration and/or composition in the plant or plant part.

In some embodiments, the content and/or composition of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. Moreover, in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art and discussed briefly, supra.

In general, concentration or composition is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or after growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds, which activate expression from these promoters, are well known in the art. In preferred embodiments, the polypeptides of the present invention are modulated in monocots, particularly maize.

Molecular Markers

The present invention provides a method of genotyping a plant comprising a polynucleotide of the present invention. Optionally, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp.7–21.

The particular method of genotyping in the present invention may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or restriction enzyme treated (e.g., Pst I) genomic clones. The length of the probes is discussed in detail, supra, but is typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res*15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. WO 96/19256. See also, Zhang, J.-H., et al. *Proc. Natl. Acad. Sci. USA* 94:4504–4509 (1997). Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased $K_m$ and/or increased $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention; and, (b) a consensus sequence of at least three homologous polynucleotides or polypeptides, respectively, of the present invention. The generic sequence of the present invention comprises each species of polypeptide or polynucleotide embraced by the generic polypeptide or polynucleotide, sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phylums, or kingdoms. For example, a polynucleotide having a consensus sequences from a gene family of *Zea mays* can be used to generate antibody or nucleic acid probes or primers to other Gramineae species such as wheat, rice, or sorghum. Alternatively, a polynucleotide having a consensus sequence generated from orthologous genes can be used to identify or isolate orthologs of other taxa. Typically, a polynucleotide having a consensus sequence will be at least 9, 10, 15, 20, 25, 30, or 40 amino acids in length, or 20, 30, 40, 50, 100, or 150 nucleotides in length. As those of skill in the art are aware, a conservative amino acid substitution can be used for amino acids, which differ amongst, aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST algorithm's smallest sum probability (P(N)). Various suppliers of sequence-analysis software are listed in chapter 7 of *Current Protocols in Molecular Biology*, F. M. Ausubel et al., Eds., Current Protocols, a joint venture between Greene Publishing Associates, Inc. and John Wiley & Sons, Inc. (Supplement 30). A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich,) SEQUENCHER. Conveniently, default parameters of such software can be used to generate consensus or generic sequences.

A Transient Expression System for Finding Defense Activators

Expression of NPR-1 dependent pathogenesis-related (PR) genes such as PR1 has been correlated with resistance to virulent bacterial and fungal pathogens. Therefore, PR genes are often used as molecular markers in defining putative activators involved in the systemic acquired resistance (SAR) signal transduction pathway. Northern and/or Western analysis data of PR genes can be used to evaluate the effects of putative activators on the expression of these genes, but it is very time consuming. A better alternative than Northern and/or Western analysis is the present invention, which provides for a faster method of screening putative defense activators in a transient expression system.

Briefly, the transient expression system is performed by introducing two genes into a plant cell or tissue. One gene is a putative activator of the defense pathway operably linked to a constitutive promoter. The other gene is a scorable marker gene operably linked to an inducible promoter. If the putative activator does activate the defense pathway, the scorable marker gene will be expressed.

The genes maybe introduced into the plant cell by a variety of methods such as but not limited to biolistic particle acceleration, Agrobacterium-mediated transformation, microinjection, direct gene transfer, and electroporation. For a complete discussion on various methods of plant transformation, please see the section entitled "Transfection/Transformation of Cells" of the present application.

Scorable marker genes are available in the art. Scorable marker genes should ideally exhibit low background activity and should not have any detrimental effects on metabolism. The scorable marker gene products will have moderate stability in vivo, so that down-regulation of gene expression as well as gene activity will be detected. Finally, the scorable marker gene should be able to be assayed by a quantitative, sensitive, simple to perform and inexpensive system.

Scorable marker genes are known in the art and include but are not limited to: Beta-glucuronidase (GUS) gene (Jefferson et al., *In Plant Molecular Biology Manual* (Gelvin et al., eds.), pp. 1–33, Kluwer Academic Publishers (1991)). This gene is encoded by the uidA locus of *E. coli*. GUS enzyme activity can be assayed easily and sensitively in plants. The expression of GUS gene fusions can be quantified by fluorometric assay, and histochemical analysis can be used to localize gene activity in transgenic tissues.

Luciferase (DeWet et al., *Mol. Cell. Biol.* 7:725–737 (1987)). Luciferase catalyzes the oxidation of D(−)-luciferin in the presence of ATP to generate oxyluciferin and yellow-green light.

Anthocyanins (Goff et al., *EMBO J* (9:2517–2522 (1990). Anthocyanin induction is a reporter system that does not require the application of external substrates for its detection. The anthocyanin system can utilize the C1, Bz and R genes, which code for transacting factors that regulate the anthocyanin biosynthetic pathway in maize seeds. The introduction of these regulatory genes under the control of constitutive promoters includes cell-autonomous pigmentation in non-seed tissues. The one preferred example of an anthocyanin reporter gene is CRC which contains a fusion of the two maize regulatory genes R and C1. (Ludwig, et al, *Proc. Natl. Acad. Sci. U.S.A.* 86:7092–7096 (1989); Paz-Ares, et al., *EMBO J*. 6:3553–3558 (1987)). The CRC fusion gene when expressed causes cells to turn red due to anthocyanin production.

Green fluorescent protein (GFP) from the jellyfish Aequorea Victoria (Kain et al., *BioTechniques* 19:650–655 (1995) and Chiu et al., *Current Biology* 6:325–330 (1996). GFP emits bright green light when excited with UV or blue light. GFP fluorescence does not require a substrate or cofactor, is stable, and can be monitored non-invasively in living cells.

Any number of inducible promoters may be operably linked to the scorable marker gene. The promoter choice will depend on the resistance pathway of interest. Inducible promoters direct expression only when certain conditions are present. For example, pathogen inducible promoters, include those from proteins, which are induced following infection by a pathogen, such as PR proteins, SAR proteins, beta-1,3-glucanase, chitinase, etc. For an extensive discussion on inducible promoters, please see the section entitled "Recombinant Expression Cassettes" in the present specification. Therefore, to determine an activator of the pathogen induced resistance pathway a pathogen inducible promoter would be used. Of particular interest is the inducible promoter for the maize PR1#81 gene, whose expression is induced by the pathogen *Fusarium moniliforme*. (Please see PCT published application No. WO 99/43819.) Other pathways of interest may include pathways expressed during insect feeding, wounding, environmental stresses such as drought, cold or heat, anaerobic conditions, and the like. Inducible promoters that are responsive to any of these conditions may be used in the present invention to find activator genes.

EXAMPLE 1

This example describes the construction of the cDNA libraries.

Total RNA was isolated from corn tissues with TRizol Reagent (Life Technology Inc. Gaithersburg, Md.) using a modification of the guanidine isothiocyanate/acid-phenol procedure described by Chomczynski and Sacchi (Chomczynski, P., and Sacchi, N. *Anal. Biochem*. 162, 156 (1987)). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

The selection of poly(A)+ RNA from total RNA was performed using PolyATact system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringent condition and eluted by RNase-free deionized water.

cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between of Not I and Sal I sites.

EXAMPLE 2

This example describes cDNA sequencing and library subtraction.

Individual colonies were picked and DNA was prepared either by PCR with M13 forward primers and M13 reverse primers, or by plasmid isolation. All the cDNA clones were sequenced using M13 reverse primers.

cDNA libraries subjected to the subtraction procedure were plated out on 22×22 cm$^2$ agar plate at density of about 3,000 colonies per plate. The plates were incubated in a 37° C. incubator for 12–24 hours. Colonies were picked into 384-well plates by a robot colony picker, Q-bot (GENETIX Limited). These plates were incubated overnight at 37° C.

Once sufficient colonies were picked, they were pinned onto 22×22 cm$^2$ nylon membranes using Q-bot. Each membrane contained 9,216 colonies or 36,864 colonies. These membranes were placed onto agar plate with appropriate antibiotic. The plates were incubated at 37° C. for overnight.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 40–50 minutes. The filters were placed on dry filter papers to dry overnight. DNA was then cross-linked to nylon membrane by UV light treatment.

Colony hybridization was conducted as described by Sambrook, J., Fritsch, E. F. and Maniatis, T., (in Molecular Cloning: A laboratory Manual, $2^{nd}$ Edition). The following probes were used in colony hybridization:

1. First strand cDNA from the same tissue as the library was made from to remove the most redundant clones.
2. 48–192 most redundant cDNA clones from the same library based on previous sequencing data.
3. 192 most redundant cDNA clones in the entire corn sequence database.
4. A Sal-A20 oligo nucleotide: TCG ACC CAC GCG TCC GAA AAA AAA AAA AM AM AAA (SEQ ID NO: 6), removes clones containing a poly A tail but no cDNA.
5. cDNA clones derived from rRNA.

The image of the autoradiography was scanned into computer and the signal intensity and cold colony addresses of each colony was analyzed. Re-arraying of cold-colonies from 384 well plates to 96 well plates was conducted using Q-bot.

EXAMPLE 3

This example describes identification of the gene from a computer homology search and cloning of the maize NPR1 polynucleotide and promoter.

Gene identities were determined by conducting BLAST (Basic Local Alignment Search Tool; Altschul, S. F., et al., (1993) J. Mol. Biol. 215:403–410; see also www.ncbi.nlm.nih.gov/BLAST/) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences were analyzed for similarity to all publicly available DNA sequences contained in the "nr" database using the BLASTN algorithm. The DNA sequences were translated in all reading frames and compared for similarity to all publicly available protein sequences contained in the "nr" database using the BLASTX algorithm (Gish, W. and States, D. J. *Nature Genetics* 3:266–272 (1993)) provided by the NCBI. In some cases, the sequencing data from two or more clones containing overlapping segments of DNA were used to construct contiguous DNA sequences.

A BLAST search of the Pioneer Hi-Bred Int'l Inc. proprietary database identified a sequence, 798034, as homologous to NPR1. CJRMC70, the longest fragment, was used to screen a lambda cDNA library made from 6 inch maize seedlings (genotype B73) cloned into λ Express (Stratagene; La Jolla, Calif.). Over 100 clones were isolated and purified. Clone length was estimated using PCR and 27 of the longest clones were removed by excision. Phagemids were isolated and submitted for sequencing. Each clone was sequenced in triplicate using a vector primer for the 5' end of the clone. The sequences were trimmed and assembled using Sequencher 3.0 (GeneCodes). Fifteen of the clones showed homology to NPR1. The 5'-most clone, designated 1115, was used for subsequent analysis. The maize NPR1 cDNA sequence and translated protein sequence can be found in SEQ ID NOS:1 and 2, respectively.

A genomic lambda library (Sal3a partial digest of B73 DNA cloned into λ Dash II, Stratagene) was screened with CJRMC70 and a single clone isolated. The clone was purified, amplified and subcloned (Sambrook et al., supra). Seven subclones (EcoRI4.5, EcoRI-4.5', EcoRI-5.0, SalI-2.0, SalI-6.0, NotI-3.0, and NotI-10.0) were analyzed. The ends of the subclones were sequenced using vector primers. Preliminary clones were assembled using Sequencher 3.0 and tested for homology to NPR1 using BLAST. Transposons were inserted into EcoRI-4.5, EcoRI-4.5' and SalI-6.0 using the Locus Pocus transposon insertion system (Novagen). A primer specific to the transposon was used to generate internal sequence data for each subclone. These data were assembled and new primers designed to link the resulting sequence. Data from 96 sequencing runs were assembled to form a 7789 bp continuous sequence that contains the pBK-CMV/1115 sequence and several kb of upstream and downstream sequence. The genomic clone of NPR1 is shown in SEQ ID NO: 3. The translated protein sequence of the maize NPR1 genomic clone is exemplified in SEQ ID NO: 4. The NPR1 promoter is shown in SEQ ID NO: 5.

Protein sequence homology was calculated based on PILEUP alignment of derived amino acid sequences of Arabidopsis NPR1 and maize NPR1. DNA coding-region homology was estimated from an alignment of the open reading frames based on the amino acid PILEUP alignment. The cDNA alignment showed 1,677 positions aligning (not counting the gaps) with 824 positions containing the same base (49.1% identity). The alignment of the amino acid sequences derived from the cDNA sequence of Arabidopsis NPR1 and maize NPR1 shows a total of 579 positions aligning (not counting gaps) and 222 positions (38.3% identity) with identical amino acids and 302 positions (52.2% similarity) with identical or similar amino acids.

Southern blot analysis was used to determine the copy number of the NPR1 gene. Maize genomic DNA isolated from maize inbreds A63, Al 88, and PHR47 was cut with the restriction enzymes BamHI, EcoRV, and EcoRI. Single bands were seen in the BamHI and EcoRV lanes. Double bands were seen in the EcoRI lanes. These results are consistent with NPR1 being present in the maize genome as a single copy.

EXAMPLE 4

This example describes the expression pattern of the NPR1 promoter.

RNA isolated from untreated maize tissue was used to perform Northern Blot analysis according to Sambrook et al., supra. A fragment from the NPR1 polynucleotide was used as a probe. NPR1 appears to be constitutively expressed in all tissues tested. The tissues tested were 10 day old leaves, mature blades, 8 day old kernels, V12 pith, 10 day old roots, R1 husks, V12 ligules, mature leaf sheath, pollen, unpollinated silks, shedding tassel, immature ear, immature tassel, ligules, and V12 roots.

To determine if NPR1 is upregulated in the presence of pathogens GS3 maize suspension cell culture cells were not treated, treated with water, treated with 1,000,000 *Fusarium moniliforme* spores/ml, or treated with 100 µg/ml chitosan (chitosan is a chito-oligosaccharide mixture from CarboMer Inc., #5,020,268X, Westborough, Mass.). NPR1 showed significant but transient upregulation in Fusarium-treated cells one hour after treatment. With chitosan-treated cells, NPR1 also showed significant upregulation one hour after treatment, which was reduced but still above control levels at two to six hours. Clearly, the NPR1 promoter will be important in expressing heterologous genes constitutively and in response to pathogen attack.

EXAMPLE 5

This example describes a transient expression system for screening putative activators of a plant defense pathway.

GS3 immature embryos were used as targets for co-bombardment of the following constructs: two promoter/screenable marker constructs: PR1#81::GUS (PHP15049) and Ubi::GUS (PHP10532) and one activator gene construct: Ubi::NPR1 (PHP16063). (Ubi=*Zea mays* ubiquitin promoter; PR1#81=maize PR1#81 promoter (PCT Publication No. WO 99/43819, and herein incorporated by reference); GUS=beta-glucuronidase)

The immature embryos were bombarded with a promoter/screenable marker construct either alone or co-bombarded with the activator construct. Particle preparation and DNA coating were carried out as described by Zhang et al. (*Plant Cell Report*, 19:241–250 (2000)) except for the use of tungsten (1.0 µm) particles and 20 µl of the each above construct DNA at different concentrations (PHP15049 at 0.02 µg/µl, PHP10532 at 0.002 µg/µl, and PHP16063 at 1.0 µg/µl). The concentration of DNA delivered for each bombardment was 0.12, 0.012, and 6.6 µg for PHP15049, PHP10532, and PHP16063, respectively. The DNA concentrations of the promoter/screenable marker constructs had previously been shown to give low background expression. Twelve immature embryos were used for each treatment and placed on osmotic medium (Vain et al., *Plant Cell Rep* 12:84–88 (1993)) for 16–20 hours before bombardment. The distance from the stopping screen to the target was 10 cm and bombardment was done at 650 psi with a PDS1000/He device (Bio-Rad Laboratories). The bombarded explants were histochemically stained in X-Gluc staining solution (McCabe et al., Bio/Technology, 87:923–926. 1988) for 16 hours at 37° C. beginning 24 hours after the bombardment. Visual observation of blue spots of histochemical GUS staining was used for interpretation of the transient assay results.

Three experiments were performed with twelve replications for each of the two promoter/screenable marker constructs with or without over-expression of NPR1 gene. The average numbers of blue spots from immature embryos bombarded with Ubi::GUS or PRI#81::GUS alone were 10±11 (standard deviation (SD)) and 8±9 (SD), respectively, but the numbers increased to 307±170 (SD) and 266±179 (SD) when NPR1 was co-expressed. Although particle bombardment is known to generate high data dispersion (Atienzar et al., *BioTechniques*, 28:54–58 (2000)) like the ones in this study, these results clearly indicate the effect of NPR1 of elevating expression of Ubi::GUS and PR1#81::GUS. Moreover, this effect, in the absence of chemical or pathogen induction, was also confirmed in cell suspension cultures co-bombarded with PR1#81::GUS and Ubi::NPR1. The increased expression of the PR1#81::GUS by overexpression of maize NPR1 in this transient system is in contrary to the observation by Cao et al., in *Proceed. Natl. Acad. Sci.* 95:6531–6536 (1998) in Arabidopsis transformed by Arabidopsis NPR1 (35S::NPR1). Constitutive expression of Arabidopsis NPR1 does not lead to constitutive expression of PR genes in the absence of chemical or pathogen induction.

Surprisingly, these results show that in the absence of induction, overexpression of NPR1 leads to a more than 20-fold increase in expression of not only PR1#81::GUS but also Ubi::GUS in this biolistic transient expression system. These results suggest that (1) this biolistic transient expression system can be used for quick screening of putative activators with reproducible results, (2) maize NPR1 up-regulates expression of PR1#81::GUS independent of chemical or pathogen induction in this transient system, and (3) ubiquitin may be involved in the SAR defense pathways.

EXAMPLE 6

To evaluate the effects of defense elicitors on PR1#81::GUS expression with or without overexpression of NPR1, three experiments with a total of five replications were performed. GS3 immature embryos were bombarded with either PRI#81::GUS alone or in combination with Ubi::NPR1. Twenty-four hours after bombardment the embryos were treated with either 50 g/ml of chitosan, 1 mM salicylic acid, or 0.1 mM jasmonic acid diluted in liquid osmotic medium. The embryos were then cultured at 28° C. for twenty to twenty-four hours before the histochemical GUS staining at 37° C. Visual observation of blue spots by histochemical GUS staining was used for interpretation of the transient assay results.

Figure 2:
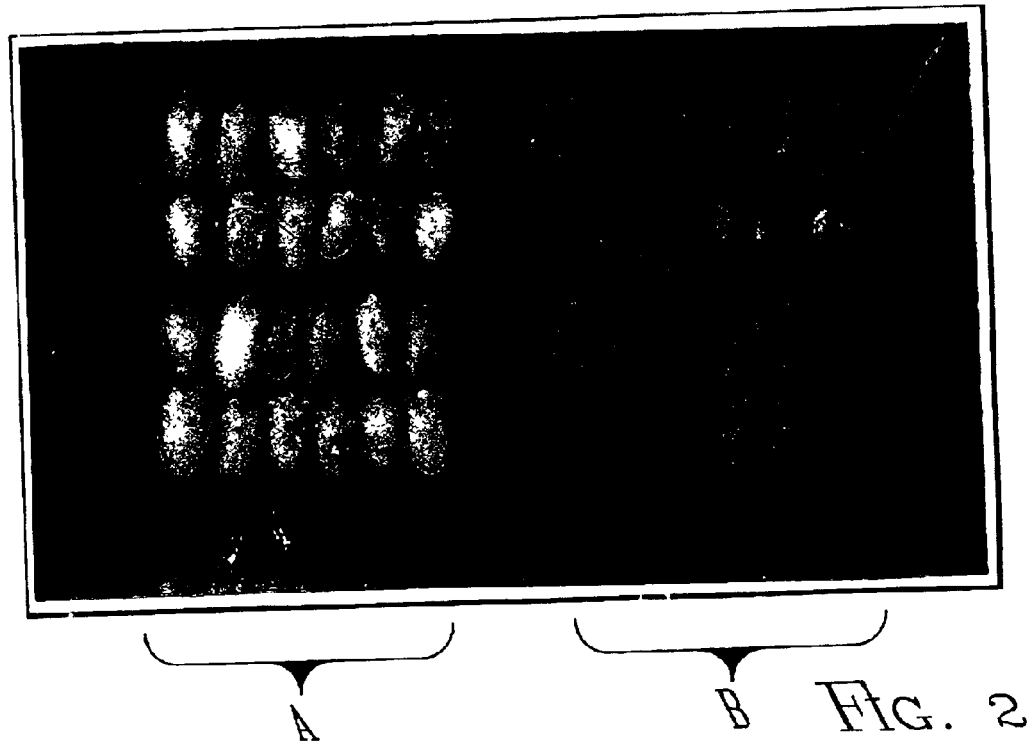
FIG. 2 depicts the results of bombarding maize GS3 embryos with PR1#81::GUS (A) and bombarding maize GS3 embryos with PR1#81::GUS and Ubi::NPR1 (B). The embryos were cultured with 50 g/ml of chitosan for twenty to twenty-four hours before histochemical GUS staining.
Figure 3:
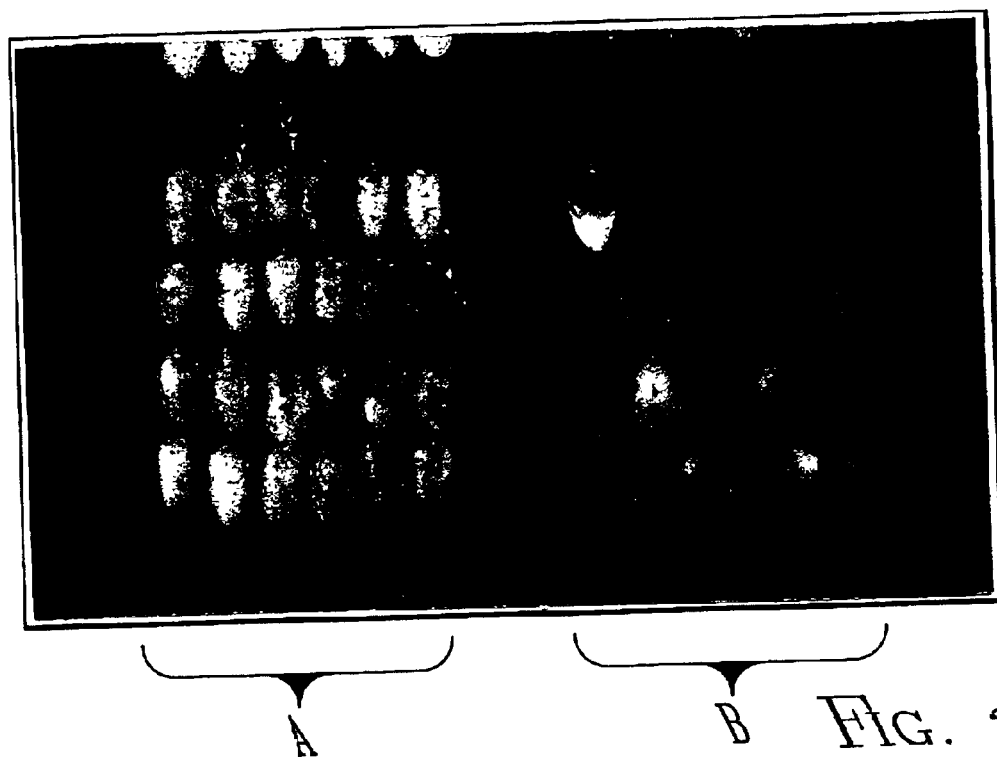
FIG. 3 depicts the results of bombarding maize GS3 embryos with PR1#81::GUS (A) and bombarding maize GS3 embryos with PR1#81::GUS and Ubi::NPR1 (B). The embryos were cultured with 1 mM salicylic acid for twenty to twenty-four hours before histochemical GUS staining.
Figure 4:
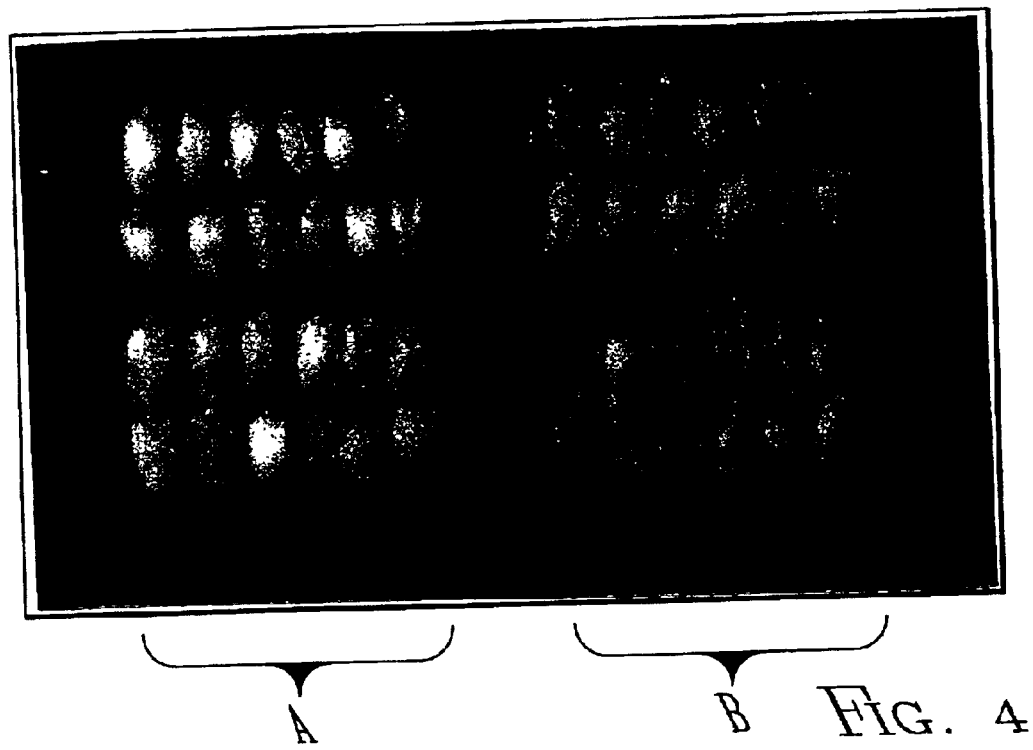
FIG. 4 depicts the results of bombarding maize GS3 embryos with PR1#81::GUS (A) and bombarding maize GS3 embryos with PR1#81::GUS and Ubi::NPR1 (B). The embryos were cultured with 0.1 mM jasmonic acid for twenty to twenty-four hours before histochemical GUS staining.

The results of the effects of the defense elicitors on PR1#81::GUS expression with or without overexpression of NPR1 can be seen in FIGS. 1 to 4. The Figures clearly show that PR1#81::GUS expression in the absence of exogenous NPR1 was up regulated by the salicylic acid treatment. This result suggests that PR1#81::GUS is indeed a reporter for a salicylic acid-dependent pathway. In addition, salicylic acid up regulates reporter expression in immature embryos in the presence of exogenous NPR1. This result suggests that NPR1 is mediating the salicylic acid-dependent expression of PR1#81::GUS.

PR1#81::GUS expression was suppressed by jasmonic acid treatment in both the presence and absence of exogenous NPR1. Salicylic acid signaling and jasmonic acid signaling pathways are interconnected in complicated ways (Glazebrook, *Curr Opin Plant Biol* 2:280–286 (1999)). Although not to be limited by theory, it has been suggested that salicylic acid signaling and jasmonic acid signaling are mutually inhibitory (Niki, et al, *Plant Cell Physiol* 39:500–506 (1998)). Therefore, these results are consistent with the theory that jasmonic acid down regulates the salicylic acid pathway.

The above examples are provided to illustrate the invention but not to limit its scope. Other variants of the invention will be readily apparent to one of ordinary skill in the art and are encompassed by the appended claims. All publications, patents, and patent applications cited herein are indicative of the level of those skilled in the art to which this invention pertains. All publications, patents, and patent applications are hereby incorporated by reference to the same extent as if each individual publication or patent application was specifically and individually indicated to be incorporated by reference.

What is claimed is:

1. An isolated nucleic acid comprising the nucleotide sequence set forth in SEQ ID NO: 5.

2. A recombinant expression cassette comprising the nucleic acid of claim 1 operably linked to a heterologous nucleic acid of interest.

3. A vector comprising the recombinant expression cassette of claim 2.

4. A host cell having stably incorporated in its genome the recombinant expression cassette of claim 3.

5. The host cell of claim 4, wherein the host cell is a plant cell.

6. A plant stably transformed with the recombinant expression cassette of claim 2.

7. Transgenic seed of the plant of claim 6, wherein the seed comprises the recombinant expression cassette.

8. A method for expressing a heterologous nucleic acid in a plant said method comprising:
   a) introducing into a plant cell or tissue a vector comprising the nucleic acid of claim 1 operably linked to a heterologous nucleic acid; and
   b) regenerating a plant from the plant cell wherein the plant expresses the heterologous nucleic acid.

9. The method of claim 8, wherein the heterologous nucleic acid is selected from the group consisting of a nucleic acid providing resistance to insects, a nucleic acid providing resistance to disease and a nucleic acid providing herbicide resistance.

10. The method of claim 9, wherein the heterologous nucleic acid is a nucleic acid providing resistance to disease.

* * * * *